(12) United States Patent
Sano et al.

(10) Patent No.: US 10,466,261 B2
(45) Date of Patent: Nov. 5, 2019

(54) AUTOMATIC ANALYSIS DEVICE

(71) Applicant: HITACHI HIGH-TECHNOLOGIES CORPORATION, Tokyo (JP)

(72) Inventors: Minoru Sano, Tokyo (JP); Akihisa Makino, Tokyo (JP); Chie Yabutani, Tokyo (JP); Rei Konishi, Tokyo (JP); Naoto Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 30 days.

(21) Appl. No.: 15/517,630

(22) PCT Filed: Sep. 18, 2015

(86) PCT No.: PCT/JP2015/076601
§ 371 (c)(1),
(2) Date: Apr. 7, 2017

(87) PCT Pub. No.: WO2016/084462
PCT Pub. Date: Jun. 2, 2016

(65) Prior Publication Data
US 2017/0328925 A1 Nov. 16, 2017

(30) Foreign Application Priority Data
Nov. 25, 2014 (JP) ................. 2014-237273

(51) Int. Cl.
*G01N 21/01* (2006.01)
*G01N 35/00* (2006.01)
(Continued)

(52) U.S. Cl.
CPC ......... *G01N 35/00732* (2013.01); *G01N 1/38* (2013.01); *G01N 21/51* (2013.01);
(Continued)

(58) Field of Classification Search
None
See application file for complete search history.

(56) References Cited

U.S. PATENT DOCUMENTS 7,842,237 B1 11/2010 Shibuya et al.
2011/0290040 A1 12/2011 Tatsutani et al.
(Continued)

FOREIGN PATENT DOCUMENTS

EP 2 339 354 A2 6/2011
JP 2000-346851 A 12/2000
(Continued)

OTHER PUBLICATIONS

English translation of JP 2009-204446 (Sep. 2009).*
(Continued)

*Primary Examiner* — Kathryn Wright
(74) *Attorney, Agent, or Firm* — Mattingly & Malur, PC

(57) ABSTRACT

The purpose of the present invention is to provide an automatic analysis device capable of efficiently performing a plurality of analyses, while reducing the footprint and cost of the device. Provided is an automatic analysis device characterized by being provided with containers for containing samples, one rack for placing the containers thereon, and a control unit, the control unit generating, with respect to the one rack, a plurality of registration patterns in which information of the positions where the containers are disposed, and information of the samples contained in the containers are correlated with each other, storing the registration patterns thus generated, applying, to the one rack, one registration pattern selected from among the registration patterns thus stored, and analyzing the samples. Also provided is an analysis method using the device.

21 Claims, 16 Drawing Sheets

(51) Int. Cl.
   *G01N 35/02* (2006.01)
   *G01N 1/38* (2006.01)
   *G01N 21/51* (2006.01)
   *G01N 21/82* (2006.01)
   *G01N 33/543* (2006.01)
   *G01N 21/77* (2006.01)
   *G01N 33/86* (2006.01)

(52) U.S. Cl.
   CPC ....... *G01N 21/82* (2013.01); *G01N 33/54313* (2013.01); *G01N 35/00* (2013.01); *G01N 35/0092* (2013.01); *G01N 35/00584* (2013.01); *G01N 35/00594* (2013.01); *G01N 35/02* (2013.01); *G01N 35/025* (2013.01); *G01N 35/026* (2013.01); *G01N 33/86* (2013.01); *G01N 2021/7769* (2013.01); *G01N 2035/00801* (2013.01); *G01N 2035/00831* (2013.01); *G01N 2035/00851* (2013.01); *G01N 2035/00891* (2013.01)

(56) References Cited

U.S. PATENT DOCUMENTS

2012/0004857 A1   1/2012   Yamato et al.
2012/0039748 A1   2/2012   Mimura et al.
2013/0034466 A1   2/2013   Wakamiya et al.
2015/0293136 A1   10/2015  Shiba et al.

FOREIGN PATENT DOCUMENTS

| JP | 2001-099840 A | | 4/2001 |
| JP | 2005-283344 A | | 10/2005 |
| JP | 2007-240223 A | | 9/2007 |
| JP | 2008-275585 A | | 11/2008 |
| JP | 2009204446 A | * | 9/2009 |
| JP | 2009-258140 A | | 11/2009 |
| JP | 2010-217057 A | | 9/2010 |
| JP | 2011-247778 A | | 12/2011 |
| WO | 01/51929 A1 | | 7/2001 |
| WO | 2014/077219 A1 | | 5/2014 |

OTHER PUBLICATIONS

International Search Report of PCT/JP2015/076601 dated Jan. 12, 2016.
Extended European Search Report received in corresponding European Application No. 15863846.0 dated Jun. 27, 2018.
Japanese Office Action received in corresponding Japanese Application No. 2018-102607 dated Jun. 11, 2019.

* cited by examiner

[Fig. 1]
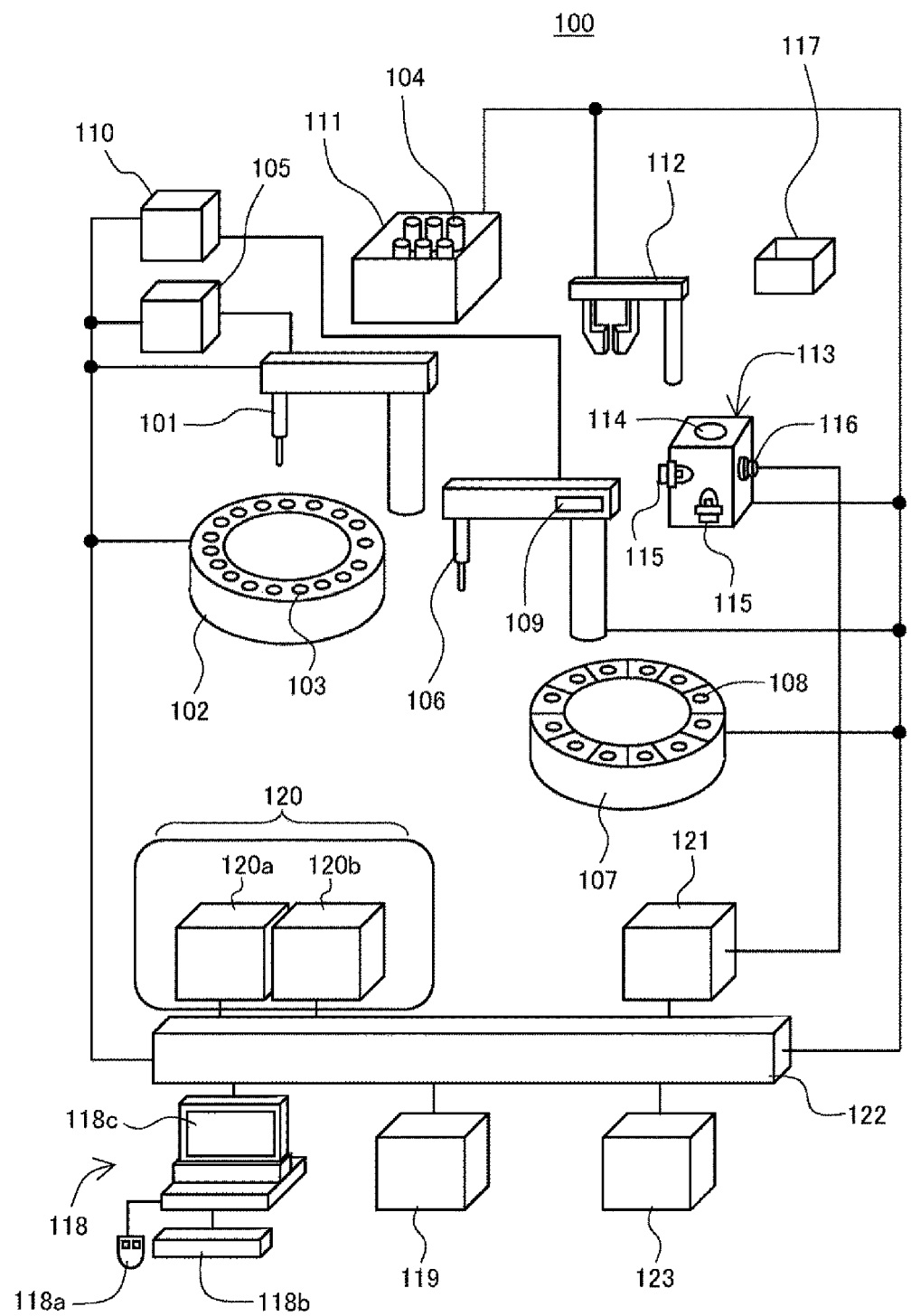

[Fig. 2]
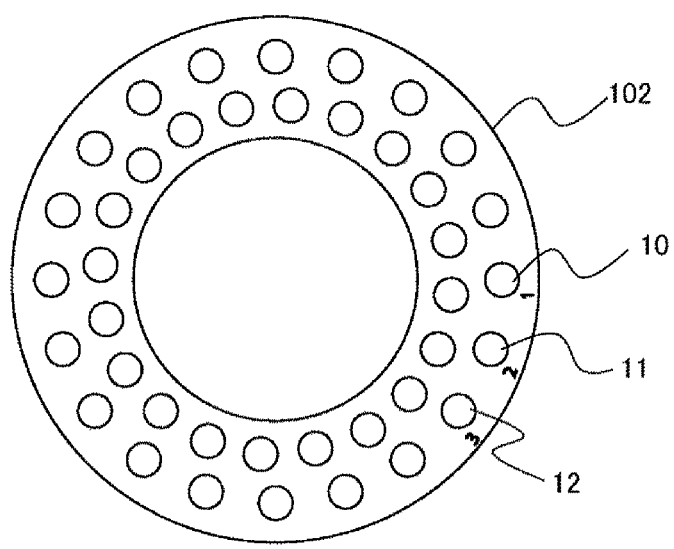

[Fig. 3A]

NAME: CALIBRATION 1

DATE OF REGISTRATION: 4/1/2014 | DATE OF CORRECTION: 4/10/2014 | DATE OF APPLICATION: 4/10/2014

| | START | END | MAJOR CLASSIFICATION |
|---|---|---|---|
| 1 | 1 | 20 | QUALITY CONTROL SAMPLE |
| 2 | 21 | 80 | CALIBRATOR |
| 3 | 81 | 90 | GENERAL SPECIMEN |
| 4 | 81 | 90 | RETEST SPECIMEN |
| 5 | 91 | 97 | FACTOR DEFICIENT PLASMA |
| 6 | 98 | 100 | CLEANING SOLUTION |
| 7 | 101 | 110 | URGENT SPECIMEN |
| 8 | | | |
| 9 | | | |
| 10 | | | |

SETTING WHEN DEVICE IS TURNED ON: AVAILABLE

| Pos. | DETAILS |
|---|---|
| 17 | QC-A |
| 18 | QC-B |
| 19 | QC-C |
| 20 | QC-D |
| 21 | Cal1 |
| 22 | Cal2 |
| 23 | Cal3 |
| 24 | Cal4 |
| 25 | Cal5 |
| 26 | Cal6 |

○ REGISTRATION PATTERN 1
○ REGISTRATION PATTERN 2
○ REGISTRATION PATTERN 3
○ REGISTRATION PATTERN 4
○ REGISTRATION PATTERN 5

APPLICATION

[Fig. 3B]

| | SPECIMEN | NUMBER OF INSTALLATIONS |
|---|---|---|
| 1 | QUALITY CONTROL SAMPLE | 20 |
| 2 | CALIBRATOR | 30 |
| 3 | FACTOR DEFICIENT PLASMA | 0 |
| 4 | COAGULATION DILUTED SOLUTION | 2 |
| 5 | GENERAL SPECIMEN | 46 |
| 6 | RETEST SPECIMEN | 10 |
| 7 | CLEANING SOLUTION | 3 |
| 8 | | |
| 9 | | |
| 10 | | |

BLOCK SETTING: 302

306 APPLICATION

[Fig. 3C]

Detailed setting: CONTROL ~307 ~304

| CONTROL | TYPE | LOT NUMBER | | | | | | |
|---|---|---|---|---|---|---|---|---|
| QC-A | SERUM | 00000001 | | | | | | |
| QC-B | SERUM | 00000002 | | | | | | |
| QC-C | PLASMA | 00000011 | | | | | | |
| QC-D | PLASMA | 00000111 | | | | | | |
| | | | | | | | | |
| | | | | | | | | |
| | | | | | | | | |

~305

| Pos. | CONTROL | TYPE | LOT NUMBER | | | | | | |
|---|---|---|---|---|---|---|---|---|---|
| 1 | | | | | | | | | |
| 2 | QC-D | PLASMA | 00000011 | | | | | | |
| 3 | | | | | | | | | |
| 4 | | | | | | | | | |
| 5 | | | | | | | | | |
| 6 | | | | | | | | | |
| 7 | | | | | | | | | |
| 8 | | | | | | | | | |
| 9 | | | | | | | | | |
| 10 | | | | | | | | | |

APPLICATION ~306

[Fig. 4]

○ REGISTRATION PATTERN 1  ● REGISTRATION PATTERN 2  ○ REGISTRATION PATTERN 3  ○ REGISTRATION PATTERN 4  ○ REGISTRATION PATTERN 5

NAME: ROUTINE 1
DATE OF REGISTRATION: 4/1/2014  DATE OF CORRECTION: 4/10/2014  DATE OF APPLICATION: 4/10/2014

APPLICATION

| | START | END | MAJOR CLASSIFICATION |
|---|---|---|---|
| 1 | 1 | 20 | QUALITY CONTROL SAMPLE |
| 2 | 21 | 40 | CALIBRATOR |
| 3 | 41 | 97 | GENERAL SPECIMEN |
| 4 | 41 | 97 | RETEST SPECIMEN |
| 5 | — | — | FACTOR DEFICIENT PLASMA |
| 6 | 98 | 100 | CLEANING SOLUTION |
| 7 | 101 | 110 | URGENT SPECIMEN |
| 8 | | | |
| 9 | | | |
| 10 | | | |

| Pos. | DETAILS |
|---|---|
| 17 | QC-A |
| 18 | QC-B |
| 19 | QC-C |
| 20 | QC-D |
| 21 | Cal1 |
| 22 | Cal2 |
| 23 | Cal3 |
| 24 | Cal4 |
| 25 | Cal5 |
| 26 | Cal6 |

[Fig. 5]

○ REGISTRATION PATTERN 1   ○ REGISTRATION PATTERN 2   ● REGISTRATION PATTERN 3   ○ REGISTRATION PATTERN 4   ○ REGISTRATION PATTERN 5

NAME: ROUTINE 2 (BIOCHEMICAL / COAGULATION)
DATE OF REGISTRATION: 4/1/2014    DATE OF CORRECTION: 4/8/2014    DATE OF APPLICATION: 4/10/2014

| | START | END | METHOD | MAJOR CLASSIFICATION |
|---|---|---|---|---|
| 1 | 1 | 10 | BIOCHEMICAL | QUALITY CONTROL SAMPLE |
| 2 | 11 | 20 | BIOCHEMICAL | CALIBRATOR |
| 3 | 21 | 50 | BIOCHEMICAL | GENERAL SPECIMEN |
| 4 | 21 | 55 | BIOCHEMICAL | RETEST SPECIMEN |
| 5 | 56 | 60 | COAGULATION | QUALITY CONTROL SAMPLE |
| 6 | 61 | 70 | COAGULATION | CALIBRATOR |
| 7 | 71 | 97 | COAGULATION | GENERAL SPECIMEN |
| 8 | 71 | 97 | COAGULATION | FACTOR DEFICIENT PLASMA |
| 9 | 71 | 97 | COAGULATION | RETEST SPECIMEN |
| 10 | 98 | 100 | COMMON | CLEANING SOLUTION |

| Pos. | DETAILS |
|---|---|
| 17 | QC-A |
| 18 | QC-B |
| 19 | QC-C |
| 20 | QC-D |
| 21 | Cal1 |
| 22 | Cal2 |
| 23 | Cal3 |
| 24 | Cal4 |
| 25 | Cal5 |
| 26 | Cal6 |

[APPLICATION]

[Fig. 6]

STATUS: REGISTRATION PATTERN 2 / UNDER ANALYSIS

○ REGISTRATION PATTERN 1   ● REGISTRATION PATTERN 2   ○ REGISTRATION PATTERN 3   ○ REGISTRATION PATTERN 4   ○ REGISTRATION PATTERN 5

NAME: ROUTINE 1
DATE OF REGISTRATION: 4/1/2014 | DATE OF CORRECTION: 4/10/2014 | DATE OF APPLICATION: 4/10/2014

[APPLICATION]   [ANALYSIS RESULT]

| | START | END | MAJOR CLASSIFICATION |
|---|---|---|---|
| 1 | 1 | 20 | QUALITY CONTROL SAMPLE |
| 2 | 21 | 40 | CALIBRATOR |
| 3 | 41 | 97 | GENERAL SPECIMEN |
| 4 | 41 | 97 | RETEST SPECIMEN |
| 5 | --- | --- | FACTOR DEFICIENT PLASMA |
| 6 | 98 | 100 | CLEANING SOLUTION |
| 7 | 101 | 110 | URGENT SPECIMEN |
| 8 | | | |
| 9 | | | |
| 10 | | | |

| Pos. | DETAILS |
|---|---|
| 17 | QC-A |
| 18 | QC-B |
| 19 | QC-C |
| 20 | QC-D |
| 21 | Cal1 |
| 22 | Cal2 |
| 23 | Cal3 |
| 24 | Cal4 |
| 25 | Cal5 |
| 26 | Cal6 |

[Fig. 7]

[Fig. 8]
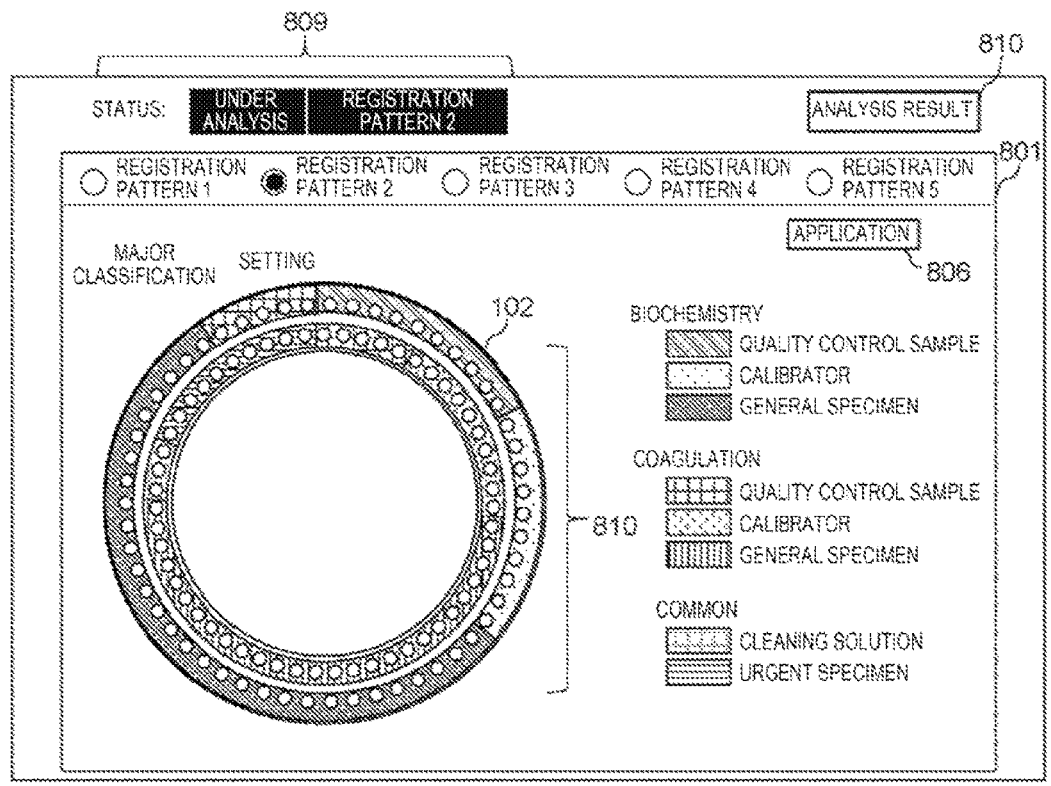

[Fig. 9]
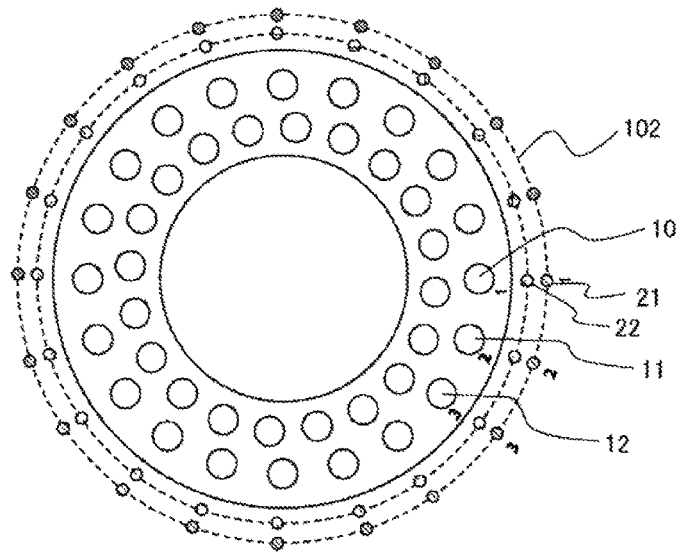
[Fig. 10]
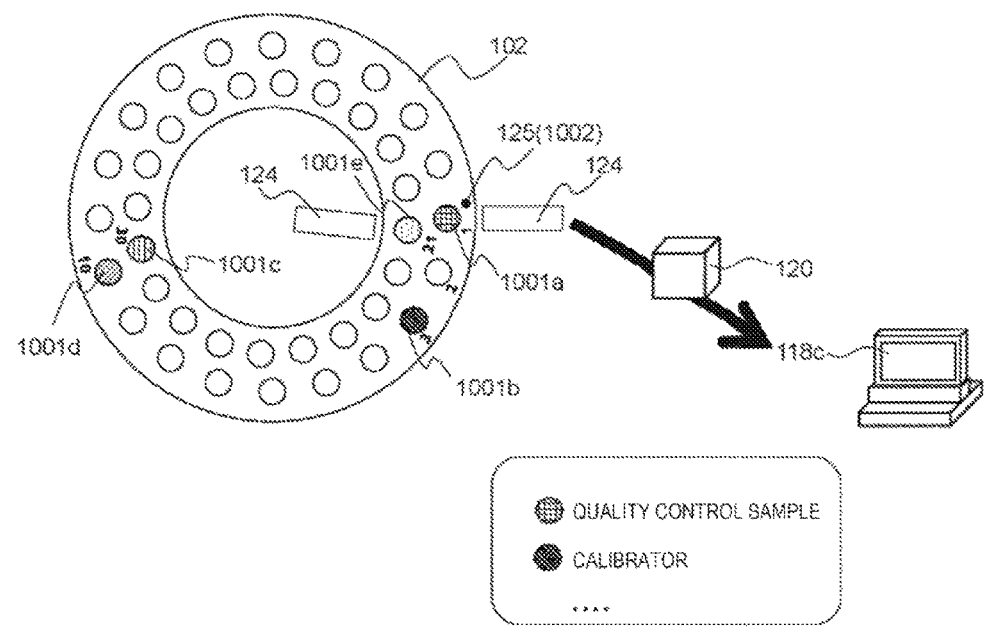

[Fig. 11]
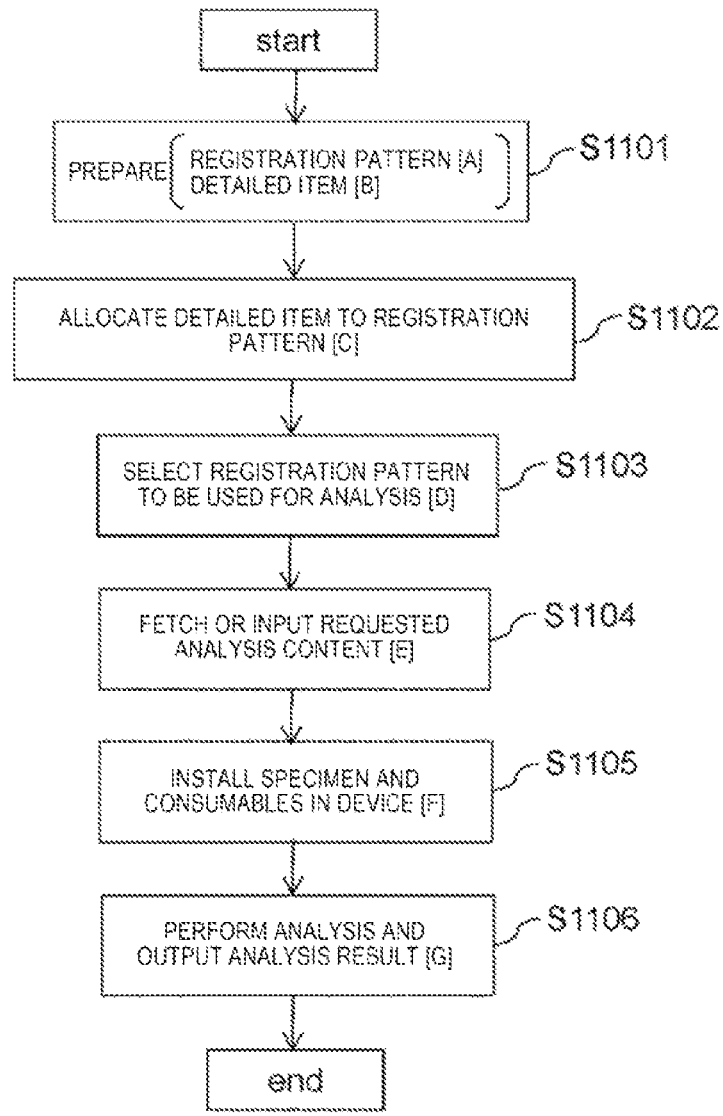

[Fig. 12]
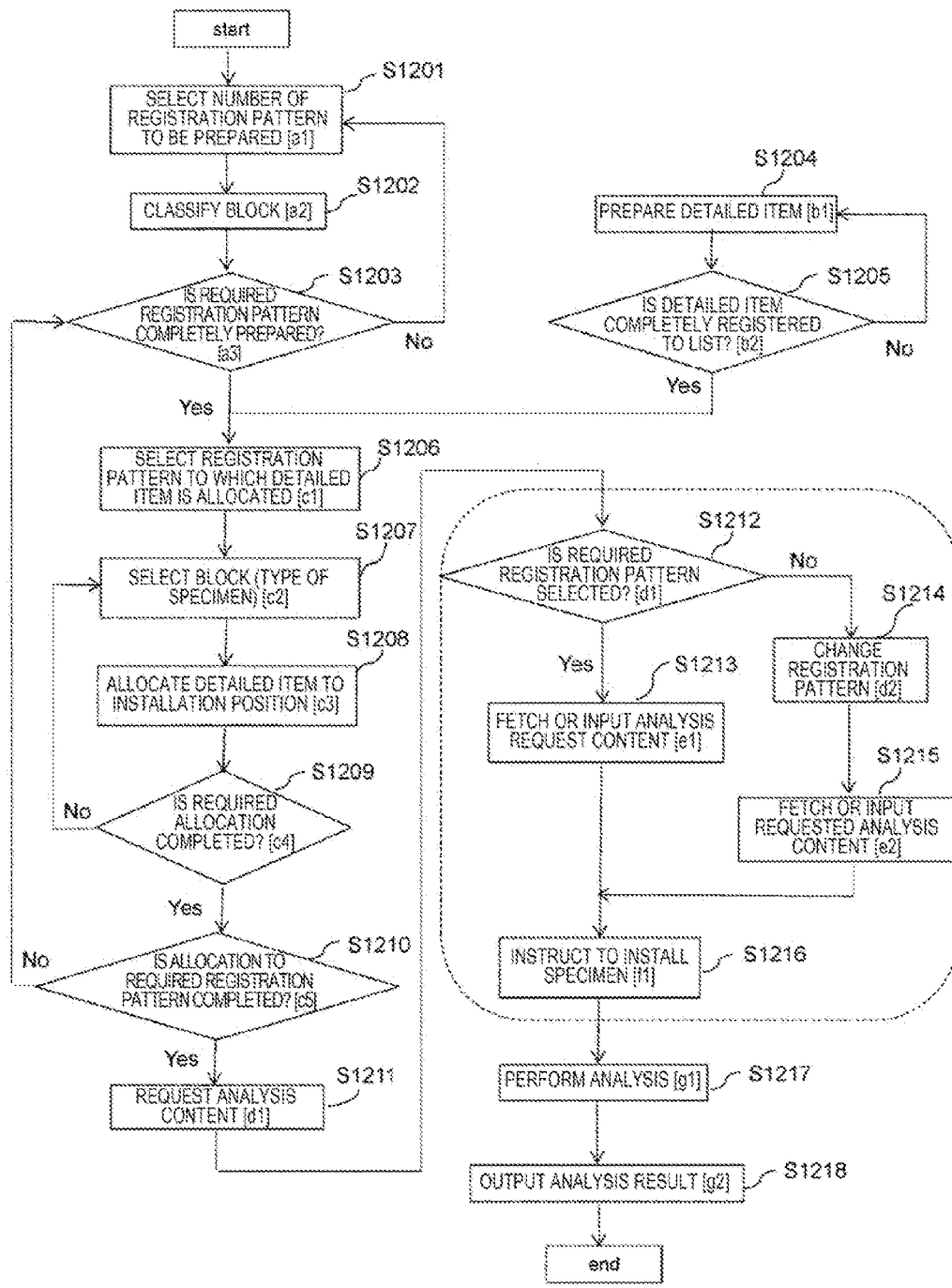

[Fig. 13]
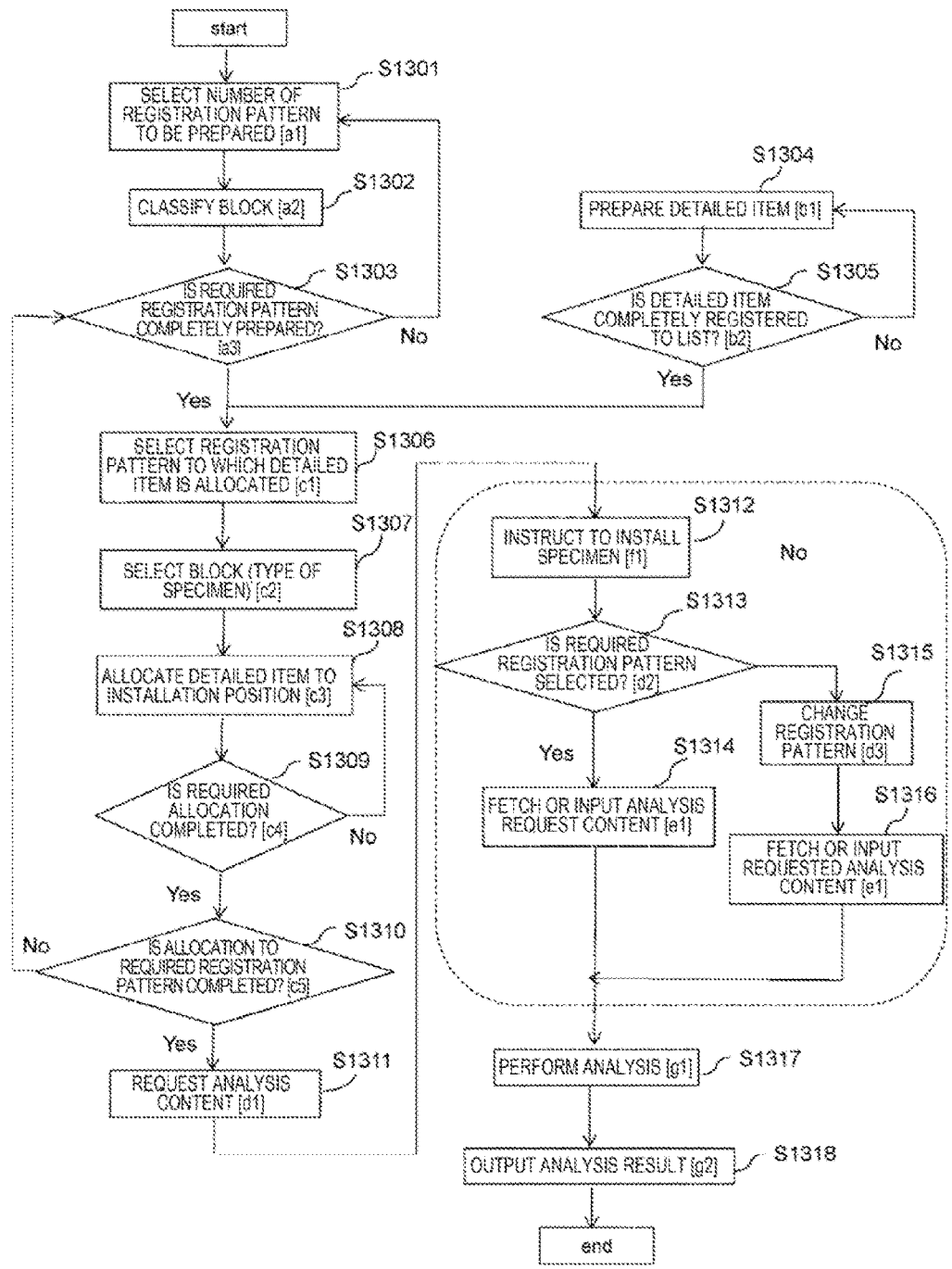

[Fig. 14]
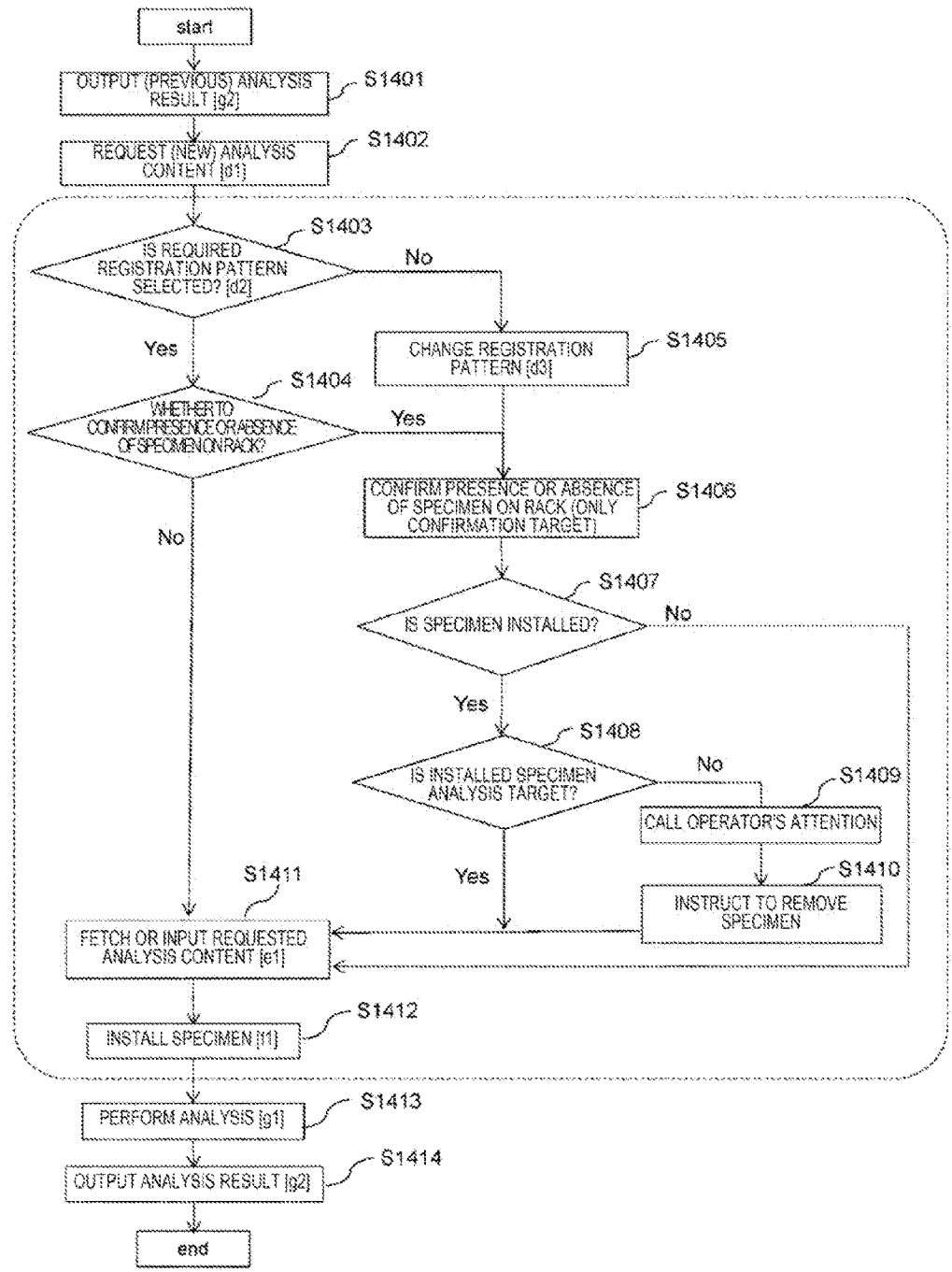

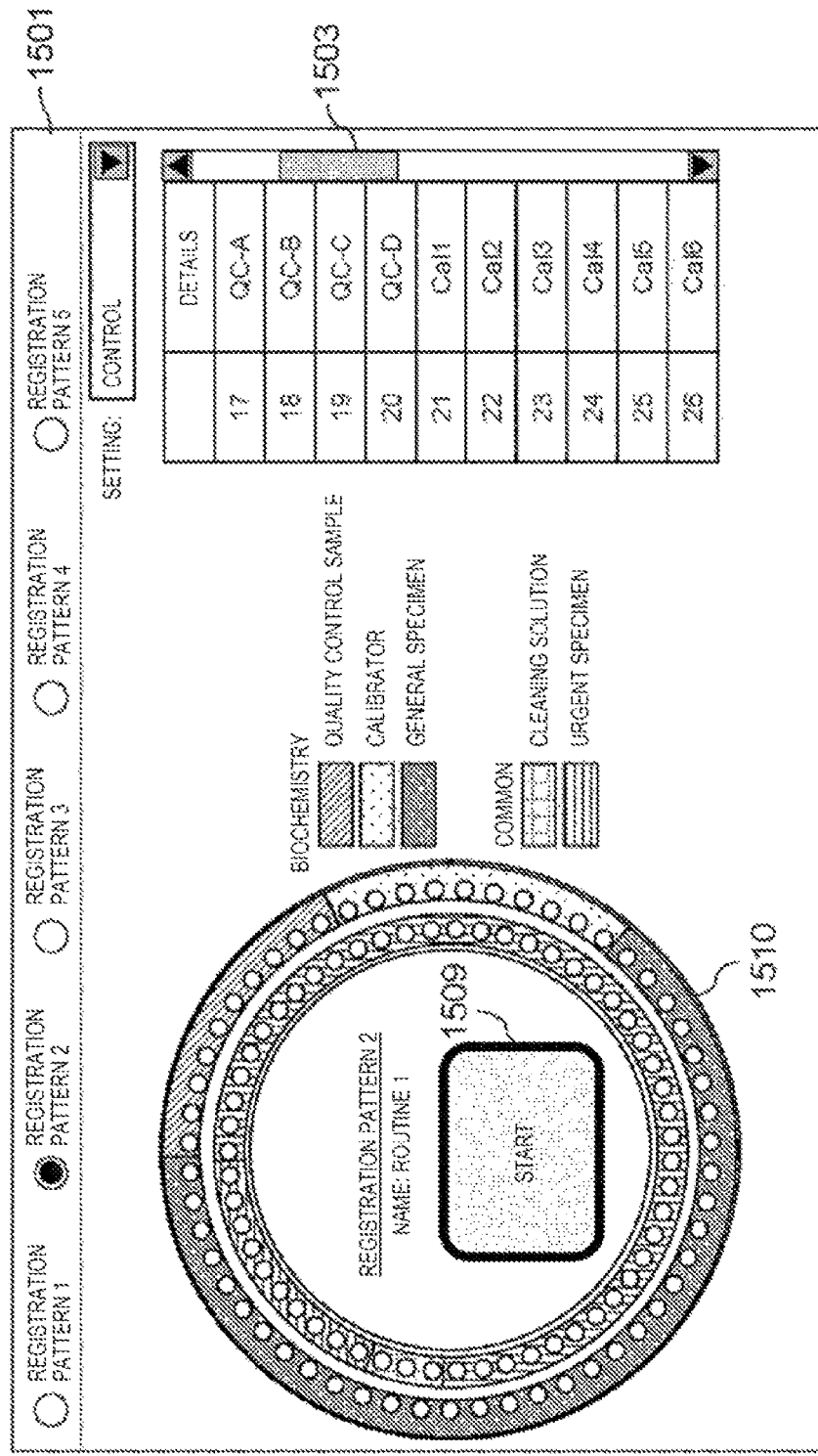
[Fig. 15]

AUTOMATIC ANALYSIS DEVICE

TECHNICAL FIELD

The present invention relates to an automatic analysis device which analyzes a component amount contained in a specimen such as blood and urine, and particularly relates to an automatic analysis device capable of measuring a biochemical test item and a blood coagulation test item.

BACKGROUND ART

As an analysis device which analyzes a component amount contained in a specimen, an automatic analysis device is known which measures intensity of transmitted light or scattered light having a single or a plurality of wavelengths obtained by emitting light from a light source to a reaction solution in which the specimen and a reagent are mixed with each other, and which calculates the component amount, based on a relationship between light intensity and density.

PTL 1 discloses the following automatic analysis device. A measurement target sample is loaded to a container such as a cup or a blood collection tube. A plurality of containers are simultaneously laid on a sample loading unit (hereinafter, referred to as a rack). The rack is placed on a sampler. In accordance with a measurement item registered in advance for each sample, the sample is dispensed from the rack to a reaction tube. In this manner, the automatic analysis device performs an analysis in accordance with each measurement item.

In PTL 1, two types of sampler such as a circular sampler and a rack sampler are described. Here, the circular sampler can be equipped with approximately several circular racks on which approximately 30 to 100 containers can be laid. On the other hand, the rack sampler can be equipped with a box-type rack on which 5 to 10 containers can be laid, in units of 10 racks by using a tray.

In addition, in PTL 1, the following technique is also described. The circular sampler is configured so that the circular racks are attachable thereto and detachable therefrom. The replaceable circular racks are managed by numbers of 1 to 9. The numbers are affixed as barcode seals. This barcode information is optically read by a rack information detection unit, and each of the racks is individually identified by a control unit.

CITATION LIST

Patent Literature

PTL 1: JP-A-2001-99840

SUMMARY OF INVENTION

Technical Problem

In recent years, as one of methods for improving efficiency of a clinical test task, functions of an automatic analysis device need to be integrated. That is, apart from a method in the related art in which a dedicated device is prepared for each different analysis method, there is provided a multi-function automatic analysis device in which a single device can perform a plurality of different analysis methods. In this manner, it is possible to provide advantages in that device management is economized, specimen management flow is simplified, and device introduction cost is reduced. On the other hand, this multi-function automatic analysis device employs a calibrator or a quality control sample required for each analysis method. Consequently, compared to the dedicated device, the number of specimens to be handled, the number of calibrators, and a type of specimens such as the quality control sample have to increase inevitably. In a case where these specimens are installed in the device via the above-described circular rack, box-type rack, and container laid on these racks, there is a physical upper limit on the number of containers which can be installed in the rack loaded in the device. Therefore, the sufficient number of specimens, calibrators, and quality control samples cannot be installed at a time, thereby interfering with a smooth test task in some cases.

However, as in the automatic analysis device disclosed in PTL 1, according to a method of using the circular rack in which it is often necessary to install relatively many containers, the size of the circular rack tends to increase. Thus, in a case where a plurality of circular racks are provided together with the automatic analysis device, it is necessary to prepare a storage place for storing the circular rack which is not in use, or a work space for installing the container in the circular rack to be used subsequent to the circular rack which is previously loaded on the automatic analysis device. Consequently, a footprint has to increase. In addition, the cost has to unnecessarily increase due to the circular rack which is not simultaneously installed in the automatic analysis device.

The present invention is made in view of the above-described problem, and an object thereof is to provide an automatic analysis device capable of efficiently performing a plurality of analyses, while reducing the footprint and cost of the device.

Solution to Problem

As an aspect for solving the above-described problem, there is provided an automatic analysis device including a container that contains the sample, one rack on which a plurality of the containers are loaded, and a control unit. The control unit prepares a plurality of registration patterns in which information of a position having the container installed therein is correlated with information of the sample to be contained in the container, for the one rack, and stores a plurality of the prepared registration patterns. The control unit applies one selected registration pattern in a plurality of the stored registration patterns to the one rack, and analyzes the sample. There is also provided an analysis method using the device.

Advantageous Effects of Invention

According to the above-described aspect, it is possible to provide the automatic analysis device and the analysis method using the device, in which a plurality of analyses can be efficiently performed while the footprint and cost of the device are reduced.

BRIEF DESCRIPTION OF DRAWINGS

FIG. 1 is a view schematically illustrating a basic configuration of an automatic analysis device according to the present embodiment.

FIG. 2 is a view schematically illustrating a basic configuration of a specimen rack according to the present embodiment.

FIG. 3A is a view for describing preparation of a registration pattern on a display unit according to the present embodiment (first embodiment).

FIG. 3B is a view for describing another example of preparation of a registration pattern on the display unit according to the present embodiment (first embodiment).

FIG. 3C is a view for describing allocation of detailed items on the display unit according to the present embodiment (first embodiment).

FIG. 4 is a view for describing further another example of preparation of a registration pattern on the display unit according to the present embodiment (first embodiment).

FIG. 5 is a view for describing preparation of a registration pattern on a display unit according to the present embodiment (second embodiment).

FIG. 6 is a view for describing application/input/confirmation of a registration pattern on the display unit according to the present embodiment (first embodiment).

FIG. 7 is a view for describing switching and application/input/confirmation of a plurality of registration patterns on the display unit according to the present embodiment (first embodiment).

FIG. 8 is a view for describing preparation of a registration pattern on a display unit according to the present embodiment (third embodiment).

FIG. 9 is a view illustrating a basic configuration of a specimen rack according to the present embodiment (fourth embodiment).

FIG. 10 is a view illustrating a basic configuration of a specimen rack according to the present embodiment (fifth embodiment).

FIG. 11 is a flowchart illustrating a basic operation performed from preparation to analysis of the registration pattern of the specimen rack in the automatic analysis device according to the present embodiment (the first embodiment).

FIG. 12 is a flowchart illustrating a basic operation in the automatic analysis device according to the present embodiment (the first embodiment) in more detail.

FIG. 13 is a flowchart illustrating another example of the basic operation in the automatic analysis device according to the present embodiment (the first embodiment) in more detail.

FIG. 14 is a flowchart illustrating an operation for detecting an error when registration patterns are switched in an automatic analysis device according to the present embodiment (seventh embodiment).

FIG. 15 is a view for describing confirmation of the registration pattern on the display unit according to the present embodiment (the first embodiment).

DESCRIPTION OF EMBODIMENTS

Hereinafter, embodiments according to the present invention will be described with reference to the drawings. Throughout the whole embodiments, description of the same respective configuration elements in each drawing may be omitted in some cases.

First Embodiment

<Basic Configuration of Device>

In the present embodiment, as an example of a multi-function automatic analysis device (hereinafter, simply referred to as an automatic analysis device or a device), a device will be described which can process an analysis item in the biochemical field or an analysis item in the blood coagulation field after a biological sample such as blood and urine (hereinafter, simply referred to as a sample) is mixed with a reagent.

FIG. 1 is a view schematically illustrating a basic configuration of the automatic analysis device according to the present embodiment.

In FIG. 1, an automatic analysis device 100 is configured to mainly include a specimen dispensing probe (sample dispensing mechanism) 101, a specimen rack 102, a reagent dispensing probe (reagent dispensing mechanism) 106, a reagent rack 107, a reaction container stock unit 111, a reaction container conveyance unit 112, a detection unit 113, a reaction container discard unit 117, an operation unit 118, a storage unit 119, and a control unit 120.

The specimen dispensing probe 101 aspirates a specimen (sample) contained in a specimen container (sample container) 103 disposed in the specimen rack 102 rotating clockwise and counterclockwise or on a quality control sample contained in a quality control sample container (not illustrated), and discharges the specimen or the quality control sample to a reaction container 104. The specimen dispensing probe 101 is connected to a specimen syringe pump 105, and is controlled by a computer serving as the control unit 120, thereby performing aspiration and discharge operations of the specimen.

The reagent dispensing probe 106 aspirates a reagent contained in a reagent container 108 disposed in the reagent rack 107, and discharges the reagent to the reaction container 104 containing the specimen. Here, a mixed solution of the specimen (including a dilution of the specimen) and the reagent is referred to as a reaction solution. The reagent dispensing probe 106 is connected to a reagent syringe pump 110, and is controlled by the computer serving as the control unit 120, thereby performing aspiration and discharge operations of the reagent.

Here, in order to analyze the blood coagulation field, the reagent dispensing probe 106 can be internally equipped with a reagent temperature raising mechanism 109. The control unit 120 controls the reagent temperature raising mechanism 109. In this manner, the temperature of the reagent aspirated by the reagent dispensing probe 106 is raised, and the reagent is adjusted to have a suitable temperature (predetermined temperature).

The reaction container conveyance unit 112 is used in order to convey and install the reaction container 104. The reaction container conveyance unit 112 pivots in a horizontal direction while holding the reaction container 104, thereby conveying and installing the reaction container 104 from the reaction container stock unit 111 to the reaction container installation unit 114 of the detection unit 113.

The detection unit 113 has one or more (in the present embodiment, a case where one is provided is illustrated as an example) reaction container installation units 114 for loading the reaction container 104. The detection unit 113 measures light intensity of the reaction container 104 inserted into the reaction container installation unit 114. In the present embodiment, a case where one detection unit 113 is provided is illustrated. However, without being limited thereto, a configuration having a plurality of detection units 113 may be adopted.

A light source 115 of the detection unit 113 emits light to the reaction container 104. The light emitted from the light source 115 is attenuated by and transmitted through the reaction solution contained inside the reaction container 104, or is scattered therein. A detection unit (optical sensor) 116 is configured to include a photodiode. The detection unit 116 receives the transmitted light which is attenuated by and transmitted through the reaction solution inside the reaction container 104 or the scattered light which is scattered therein, and performs light/current conversion, thereby outputting a measurement light signal indicating the light intensity of the received light to an A/D converter 121. The measurement signal of the transmitted light or the scattered light which is A/D converted by the A/D converter 121 is input to the control unit 120 via an interface 122. An operation of the detection unit 113 is controlled by the computer serving as the control unit 120.

The reaction container conveyance unit 112 holds the reaction container 104 for which measurement is completed, and conveys the reaction container 104 to a reaction container discard unit 117 so as to be discarded.

The analysis item of the sample which is analyzed by the automatic analysis device 100 is input to the control unit 120 from the operation unit 118 via a keyboard 118b serving as inputting means or an operation screen displayed on a display unit 118c. A configuration may be adopted which uses a graphical user interface (GUI) for inputting the analysis item by causing a mouse 118a to operate a pointer so as to input the analysis item displayed on the display unit 118c.

Here, the control unit 120 will be described. The control unit 120 is configured to mainly include an overall control unit 120a and a measurement control unit 120b.

The overall control unit 120a controls an operation of the automatic analysis device 100 such as dispensing the sample or the reagent, transferring the reaction container 104, and discarding the reaction container 104 which are described above.

The measurement control unit 120b performs a calculation process on a measurement value of the light intensity which temporally varies in response to a degree of mixed reaction between the sample and the reagent. Based on a calibration value acquired in advance, the measurement control unit 120b calculates concentration of an analysis target or a reaction time (indicating a coagulation time in the blood coagulation field). In addition, based on a result of comparison with a predetermined determination threshold, the measurement control unit 120b can determine quality by determining the concentration or the reaction time of the analysis target included in the sample. The calculated concentration or reaction time is output to the display unit 118c, and is stored in the storage unit 119. The concentration or reaction time obtained as a calculation result may be printed out by a printer 123 via the interface 122.

<Basic Configuration of Specimen Disk>

FIG. 2 is a view schematically illustrating a basic configuration of the specimen rack 102 according to the present embodiment.

In FIG. 2, numbers serving as position information are allocated sequentially from 1 at an installation position for installing the specimen container 103, and an installation position 1 (10), an installation position 2 (11), and an installation position 3 (12) are illustrated as representative positions. The drawing illustrates a configuration in which the specimen rack 102 is provided with 20 installation positions for each of both the inner periphery and the outer periphery.

<Regarding Operation Flow>

A basic operation flow according to the present embodiment will be described with reference to FIGS. 11 to 13.

FIG. 11 is a flowchart illustrating the basic operation performed from preparation to analysis of a registration pattern of the specimen rack in the automatic analysis device according to the present embodiment.

This operation flow is performed by under the control of the control unit 120. Here, a schematic operation in each step will be described with reference to the drawing, but details will be described with reference to FIG. 12. The registration pattern means information in which information relating to the installation position of the specimen container 103 in the specimen rack 102 is correlated with information relating to the specimen contained in the specimen container 103.

In Step 1101, the registration pattern and a detailed item are prepared for the specimen rack 102 (S1101). Here, for example, the detailed item means an individual item in each process performed for QC or calibration analysis. For example, a QC process is classified in more detail such as QC-A, QC-B, and the like in accordance with content thereof. Here, any one of the registration pattern and the detailed item may be prepared earlier. Any configuration is applicable so as to change the order in accordance with analysis or various statuses. A plurality of registration patterns can be prepared such as registration patterns 1, 2, 3, and the like (to be described later). Hereinafter, a method of selecting one in accordance with the analysis by preparing the plurality of registration patterns will be described. However, only a single registration pattern can also be prepared.

Next, in Step 1102, the detailed items prepared in Step 1101 are allocated so as to correspond to each installation position determined by the registration pattern (S1102).

In Step 1103, the registration pattern to be used for the analysis is selected from the registration patterns whose detailed items are allocated in Step 1102 (S1103).

In Step 1104, content of a requested analysis is fetched or input (S1104). For example, the analysis content includes a biochemical analysis and a blood coagulation test.

Next, in Step 1105, based on the analysis content fetched or input in Step 1104, consumables such as required specimens, samples, and various containers are installed in the automatic analysis device (S1105). Here, an operator may install the consumables by the control unit 120 causing the display unit 118c to display an instruction of the operator. Alternatively, the device can cause a moving mechanism of the sample container to automatically install the consumables.

If the above-described installation is completed, the requested analysis is performed, and the obtained analysis result is output (S1106).

FIG. 12 is a flowchart illustrating a basic operation in the automatic analysis device according to the present embodiment in more detail. Respective operations illustrated in FIG. 11 will be described in more detail with reference to the drawing. Here, symbols A to G given to the respective operations illustrated in FIG. 11 respectively correspond to symbols a to g illustrated in the drawing. That is, for example, in more detail, the operation to which the symbol A is given in FIG. 11 includes symbols a1 to a3 in FIG. 12.

First, in Step 1201, a number of the registration pattern to be prepared is selected (S1201). For example, in a case where 6 registration patterns need to be prepared, it is selected whether any number of the registration pattern is to be prepared among Nos. 1 to 6.

Next, in Step 1202, blocks are classified (S1202). Here, the block means a region from a position of start number to a position of an end number where the quality control samples, the calibrators, and various specimens are respectively arranged at a plurality of installation positions in the specimen rack, for example.

In Step 1203, it is determined whether all of the required registration patterns are completely prepared (S1203). In a case where all of the required registration patterns are not completely prepared, processes subsequent to Step 1201 are performed on the remaining registration patterns. On the other hand, in a case where all of the required registration patterns are completely prepared, Step 1204 and Step 1205 are completely performed, the process proceeds to Step 1206.

Here, in Step 1204, the above-described detailed items are prepared (S1204). In Step 1205, all of the detailed items are prepared, and it is determined whether all of the detailed items are completely registered to a list (S1205). In a case where all of the detailed items are not completely registered, the remaining detailed items are prepared in Step 1204. On the other hand, in a case where all of the detailed items are completely registered to the list, the process proceeds to Step 1206.

Here, any one may be performed earlier in the preparation [a1 to a3: corresponding to A in FIG. 11] of the registration patterns in Step 1201 to Step 1203 and the preparation [b1 and b2: corresponding to B in FIG. 11] of the detailed items in Step 1204 to Step 1206. When both the preparations are completed, Step 1206 starts.

In Step 1206, the registration pattern to which the prepared detailed items are allocated is selected (S1206).

For example, in a case where 6 registration patterns are prepared, it is selected whether to allocate the detailed item to any number of the registration pattern among the numbers 1 to 6.

In Step 1207, the block classified in Step 1202, which corresponds to the specimen of a target type, is selected (S1207). In Step 1208, the detailed items are allocated to the selected block in units of respective installation positions (S1208).

In Step 1209, it is determined whether all of the required detailed items are completely allocated (S1209). In a case where all of the required detailed items are not completely allocated, Step 1207 is performed again.

In a case where all of the required detailed items are completely allocated to the registration patterns selected in Step 1206, it is determined whether the detailed items are completely allocated to all of the required registration patterns (S1210). In a case where the detailed items are not completely allocated, the process returns to Step 1203. Those which require the allocation are selected from the remaining registration patterns, and the same process is performed.

On the other hand, in a case where the detailed items are completely allocated to all of the required registration patterns, in Step 1211, the analysis content is requested (S1211). In Step 1212, it is determined whether the required registration patterns are selected in accordance with the analysis content (S1212).

Here, in a case where the required registration patterns are selected, the analysis content requested in Step 1213 is fetched or input (S1213). On the other hand, in a case where the required registration patterns are not selected, in Step 1214, the registration patterns are changed to those which are required (S1214). In Step 1215, the requested analysis content is fetched or input (S1215).

Thereafter, an operator is instructed to install the specimen in accordance with the analysis content requested in Step 1216, or the specimen is automatically installed as described above (S1216). If the specimen is completely installed, an analysis is performed in Step 1217 (S1217), and an analysis result obtained in Step 1218 is output (S1218).

FIG. 13 illustrates a modification example of the flowchart illustrated in FIG. 12. Steps 1301 to 1311 and Steps 1317 and 1318 respectively correspond to Steps 1201 to 1211 and Steps 1217 and 1218 which are illustrated in FIG. 12, and thus, description thereof will be omitted. Here, in Step 1312, an operator is instructed to install the specimen in accordance with the analysis content requested in Step 1311 (S1312). If the specimen is completely installed, it is subsequently determined whether the required registration patterns are selected in Step 1313 (S1313). In a case where the required registration patterns are selected, the analysis content requested in Step 1314 is fetched or input (S1314). On the other hand, in a case where the required registration patterns are not selected, in Step 1315, the registration patterns are changed to those which are required (S1315). In Step 1316, the requested analysis content is fetched or input (S1316).

Here, as a matter of course, in an example other than the example of the flowchart as described with reference to FIGS. 12 and 13, the procedure can also be appropriately changed in actual practice.

<Regarding Display Screen>

FIGS. 3 to 5 are views schematically illustrating the display unit 118c according to the present embodiment. FIG. 3A is a view for describing the preparation of the registration pattern on the display unit according to the present embodiment. FIG. 3A illustrates an example in which the display unit 118c causes a registration pattern display unit 301 to select and display 5 different registration patterns of specimen information from a registration pattern 1 to a registration pattern 5. As the specimen information, a number of the installation positions of at least the specimen rack 102 and a type of the specimen allocated thereto are registered, and these are displayed on a specimen information display unit 302. For example, in a case where the installation positions of the specimen rack 102 are provided from No. 1 to No. 110, the installation positions of the quality control sample, the calibrator, various specimens, and the cleaning solution are registered by classifying the blocks using the start number and the end number of the installation positions. Here, the registration pattern display unit 301 or the specimen information display unit 302 for displaying the specimen information relating to the selected registration pattern can always display the registration pattern or the specimen information even during the analysis operation.

FIG. 3B is a view for describing another example of the preparation of the registration pattern on the display unit according to the present embodiment.

In addition to the above-described example, as illustrated in FIG. 3B, as a registration method of the block, an operator inputs the number of registered specimens such as the quality control samples and the calibrators to the specimen information display unit 302. In this manner, the device can automatically allocate the start number and the end number in good order in accordance with the number of registered specimens.

A form of the display unit 118c illustrated in FIG. 3A shows the registration pattern suitable for a status where the calibration of analysis performance is mainly performed during a cycle of a series of test tasks. A name of "Calibration 1" is registered in "Registration Pattern 1" which is an identification name of the first registration pattern. The identification name of the registration pattern is displayed on an identification number display unit 308. Instead of the identification name of the registration pattern, the identification number such as simply "1" and "2" may be used. The registration pattern and the identification name can be optionally prepared or deleted by an operator, and the name can be optionally determined or selected by the operator.

As illustrated in FIG. 3A, the quality control samples can be installed at installation positions Nos. 1 to 20, and the calibrators can be installed at installation positions Nos. 21 to 80. In addition, the specimens can be classified into a general specimen, a retest specimen whose validity of a retest is recognized for some reasons based on a result of the first test, and an urgent specimen to be analyzed by being interposed in a general specimen group whose analysis item or order is scheduled in advance, since an urgent test is required. However, in FIG. 3A, any one of the general specimen and the retest specimens can be installed in the same block at the installation positions 81 to 90. In addition, the specimens such as the factor deficient plasma and the coagulation dilution which are used for the blood coagulation test can be installed at the installation position Nos. 91 to 97. Furthermore, a cleaning solution used in cleaning a specimen dispensing probe can be installed at the installation position Nos. 98 to 100.

As described above, after the installation positions are classified as information of consecutive positions from the start number to the end number, detailed information is further registered in each classification. For example, at the installation positions Nos. 1 to 20 of the quality control sample, a type of the quality control sample can be allocated to each number from Nos. 1, 2, and 3 to No. 20. The identification information of the quality control sample can be registered at each position. Similarly, with regard to the calibrator, a type of the calibrator can also be allocated to each installation position, and the identification information can be registered at each installation position. At the installation position Nos. 81 to 90 of the general specimen or the retest specimen and the installation position Nos. 101 to 110 of the urgent specimen, it is possible to input the identification information such as the specimen number associated with patient information and analysis information of the analysis item.

In addition, a detailed item display unit 303 can set and display the above-described more detailed item for major classification, otherwise referred to herein as "classification".

FIG. 3C is a view for describing the allocation of the detailed items on the display unit according to the present embodiment. In FIG. 3C, the quality control sample (displayed as Control or QC in the drawing) can be registered in advance to a list displayed on a registration list display unit 304 illustrated on the left side of the drawing. The quality control sample can be allocated to the installation position (displayed as Pos. in the drawing) displayed on an installation position allocation display unit 305 prepared using in a table form on the right side in the drawing. A target for setting the detailed item can be selected by a detailed item setting target display unit 307.

As described above, after the blocks are determined through the major classification of the quality control sample or the calibrator, detailed identification information is registered to each installation position of each block. Accordingly, in a case where the same registration pattern needs to be registered again to the installation position which is not suitable for the block having the specimen set therein, the detailed identification information can be registered after the block is first registered again.

In addition to the above-described example, as a more operator-friendly function, in order for an operator to install the specimen at a position which does not match the set block, the operator registers the detailed identification information. In accordance with the identification information, the device asks the operator whether or not to correct the block. In a case where the operator agrees correcting the block, the block can be automatically changed.

In a case where the detailed identification information is newly registered to the installation position away from the block matching the specimen as far as two or more blocks, the installation position to be newly registered and the installation position present between the blocks already registered can also be registered again to the blocks of the same type at the same time. The reason is as follows. For example, in a case where the installation positions of the quality control sample are classified into the block Nos. 1 to 10 and the installation positions of the calibrator are classified into block Nos. 11 to 20, and in a case where the calibrator is to be newly registered to the installation position of No. 5, if the detailed identification is registered, the block is updated to the calibrator in the matching block. Alternatively, the block Nos. 6, 7, 8, 9, and 10 interposed between the currently registered block No. 11 and the block No. 5 are correspondingly updated to the blocks of the calibrator.

In this case, in the detailed identification information whose content has already been registered and which has information such as an analysis result, the block is erased from the registration pattern due to the updated block. However, the information is secured in another storage region. Accordingly, the information can be called up and registered to another installation position of the same registration pattern under this work or other registration patterns In this way, individual detailed identification information which can store detailed information is secured in a common storage region. The individual detailed identification information can be freely called up to each registration pattern, and can be registered and erased. When the block is changed on the registration pattern, each data to be erased from the setting or the screen can be called up from the common storage region. The data can be called up and registered to other setting positions or other registration patterns.

In accordance with this detailed information, the device determines the required specimen. The classification of the calibrator or the general specimen is automatically input to the device.

According to this configuration, the registration pattern can be more quickly prepared. The individual calibration result or the quality control result is associated with the number or the name of the detailed information. The mouse 118a is used to select the detailed information, and the detailed information is switched to a separate display screen (not illustrated), thereby enabling an operator to confirm the result.

In addition, restrictions may be set so that the installation positions Nos. 101 to 110 of the urgent specimen cannot be changed. Without depending on timing at which the urgent specimen is carried into a laboratory, it is necessary to preferentially analyze the urgent specimen. Without depending on the registration pattern of the specimen rack 102, one determined position is always secured. In this manner, the operator can easily recognize the installation position, and can reliably install the specimen container 103 of the urgent specimen.

In addition, a shortcut button (not illustrated; hereinafter, referred to as a STAT button) for analyzing the urgent specimen can be disposed in the device. When the device is in an analyzing state, if the operator presses down the STAT button disposed in the vicinity of the specimen rack 102, the device stops dispensing a new specimen in the general specimens already installed inside the device.

In this case, the specimen already completely dispensed can be continuously analyzed. The installation positions Nos. 101 to 110 to which the urgent specimens are allocated on the specimen rack 102 are moved to a front surface of the device, thereby enabling the operator to install the urgent specimens. Subsequently, the operator instructs the device to start the analysis, thereby causing the device to preferentially analyze the installed urgent specimen and to output the result.

In addition, a method may be employed in which the specimen information is automatically input to the automatic analysis device through the identification information such as a barcode affixed to the specimen container 103, and an identification information reading device such as an optical barcode reader.

In addition, it is possible to freely set a case where the blocks are allocated to a type of one specimen and a case where the blocks are collectively allocated to a type of a plurality of specimens. As an example, if the general specimen, the quality control sample other than the general specimen, and the calibrator can be classified into a collective group, a registration method of the block can be simplified, and the registration method of the block can be further optimized according to a status where the operator uses the device.

In addition to the identification name or the registration name of the registration pattern, a manual can be additionally input to the display unit 118c via the mouse 118a or the keyboard 118b.

It is desirable to set restrictions so that the groups having the respectively classified specimens such as the calibrator and the general specimen are fixedly installed at the consecutive installation positions. In addition, it is possible to set restrictions so that the installation positions of the calibrator, the quality control sample, and the general specimen can be registered in the order of the recently provided number of the installation positions of the specimen rack 102. According to this configuration, it is possible to avoid mismatching between the specimen installed by the operator and the registration pattern.

FIG. 4 is a view for describing further another example of the preparation of the registration pattern on the display unit according to the present embodiment.

That is, a form of the display unit 118c illustrated in FIG. 4 shows the registration pattern suitable for a status where the specimen is mainly analyzed during a cycle of a series of test tasks. In an identification name display unit 408, a name of "Routine 1" is registered in "Registration Pattern 2" which is an identification name of the second registration pattern. Many calibrators are installed in "Calibration 1" described above. In contrast, "Routine 1" is characterized in that many general specimens can be installed and processed.

If an input unit such as the mouse 118a selects an application button 406 displayed on a screen displayed on the display unit 118c, the corresponding registration pattern is applied to the device. In addition, as an independent button for Nos. 1 to 5 on the device, it is possible to dispose a hardware switch correlated with the registration pattern of the specimen (not illustrated). According to this configuration, an operator can apply a desired registration pattern to the device via the input unit such as the keyboard 118b or the mouse 118c of the operation unit 118. In addition, as another means, the operator can apply a desired registration pattern to the device by pressing down a hardware switch associated with the desired registration pattern.

A display lamp using an LED corresponding to an individual hardware switch is disposed in the vicinity of the hardware switch. The display lamp is turned on or off corresponding to the registration pattern applied to the device. In this manner, the operator can confirm the applied registration pattern on the device. In this case, the registration pattern applied to the display unit 118c through the hardware switch is displayed on the display unit 118c. Accordingly, the operator can confirm the applied registration pattern by using either the display lamp of the hardware switch or the display unit 118c.

In addition, instead of the display lamp displaying the applied registration pattern, it is possible to dispose a device display unit which displays all or any one of the name, the identification number, the manual, and the content of the registration pattern (not illustrated).

If the analysis content is requested, the device instructs the operator to install the specimen by causing the display unit 118c to display the instruction. In accordance with the content of the applied registration pattern, the operator installs the specimen at the installation position of the specimen container 103 of the specimen rack 102. Alternatively, as described above, the device can automatically install the specimen. Subsequently, the operator instructs the automatic analysis device to start the analysis via the operation unit 118. After receiving the instruction, the automatic analysis device performs a positioning operation such as the rotation of the specimen rack 102, and stops the specimen container 103 containing the specimen scheduled in advance so as to be located at a specimen aspirating position of the specimen dispensing probe 101. Thereafter, the automatic analysis device sequentially aspirates the specimen, and performs the analysis operation which is a step subsequent thereto.

Timing at which the operator can apply the registration pattern to the device will be described. A state of the automatic analysis device can be roughly classified into three device state. A first state is an analysis standby state, and is a step for the operator's preparation before the analysis starts. This is a completing step of registering and installing the specimen or the reagent to be used for the analysis, registering the analysis request, and replenishing the consumables of the device. It is also possible to confirm, change, and apply the registration pattern of the specimen rack 102. In this state, the specimen to be installed in the device is likely to match the information of the specimen to be registered to the device. Accordingly, in this state, the operator can more accurately recognize the device state.

A second state is an analysis operation state. The operator inputs an analysis start instruction, thereby causing the device to perform the requested analysis process in accordance with the schedule. The installed specimens are processed sequentially or in batches. After an analysis time required for the requested analysis item elapses, analysis results are output to the display unit 118c sequentially from the specimens whose analysis results are obtained.

FIG. 6 is a view for describing application/input/confirmation of the registration pattern on the display unit according to the present embodiment. Within a frame of "State", a status display unit 609 of the display unit 118c displays "Under Analysis" showing the current device state, and "Registration Pattern 2" showing the identification name of the registration pattern used for the analysis during the process.

Here, in order to prevent the registration pattern from being erroneously recognized, the operator uses the mouse 118a to select a tab of the identification name from "Registration Pattern 2" showing the registration pattern associated with the state of "Under Analysis", thereby enabling the operator to confirm the registration content. However, restrictions are set so that the registration content cannot be changed. On the other hand, the operator uses the mouse 118a to select a tab of the identification name from "Registration Pattern 1", "Registration Pattern 3", "Registration Pattern 4", and "Registration Pattern 5" which are illustrated as other identification names. In this manner, the operator can confirm or change the registration content.

In this manner, the operator does not erroneously recognize the registration pattern applied to the current analysis and the registration pattern scheduled to be applied to the subsequent analysis. In addition, even if the device is under the analysis operation, the operator can input and set the registration pattern scheduled to be applied to the subsequent analysis. Therefore, the device can be efficiently used.

In addition, a link is set on a screen so that a screen for confirming or setting the registration pattern can be easily switched to a screen for displaying the analysis result or a screen for displaying the device state. If the operator uses the mouse 118a to select an analysis result display button 610 of the display unit 118c, the obtained analysis result or the device state is displayed. In addition, the link is also set so that the screens can be easily switched therebetween in a case where the screen for displaying the analysis result or the device state returns to the screen for displaying the registration pattern.

As a further expanded function, a schedule function can be provided so as to correspond to the process of various and many specimens. This function can correspond to a case where a single registration pattern has insufficient items in performing the requested analysis and a plurality of registration patterns are switched therebetween and applied to the device.

Figure 7:
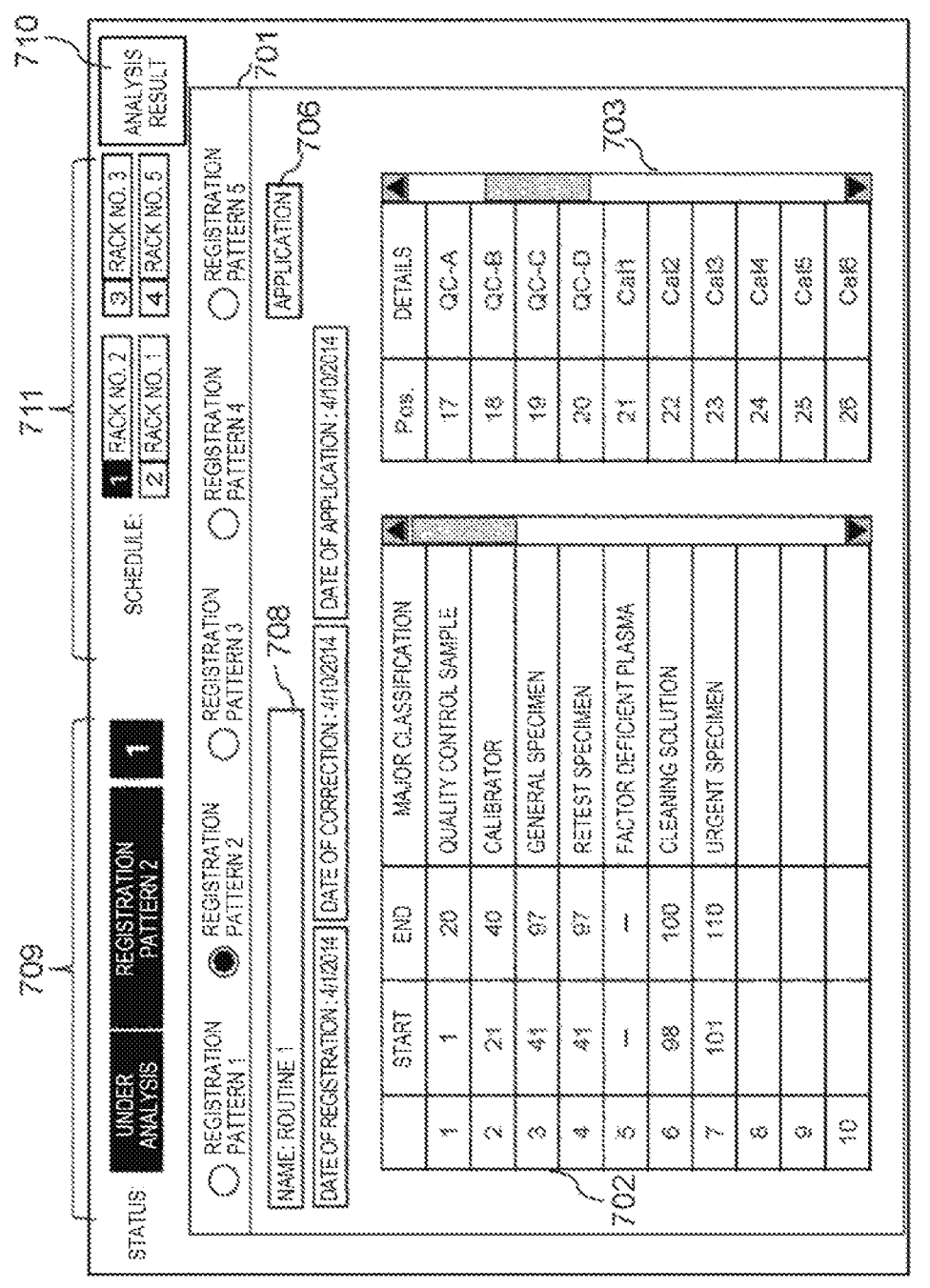

Here, FIG. 7 is a view for describing switching and application/input/confirmation of the plurality of registration patterns on the display unit according to the present embodiment. Within a frame of "State", a status display unit 709 of the display unit 118c displays "Under Analysis" showing the current device state, "Registration Pattern 2" showing the identification name of the registration pattern used for the analysis during the process, and the number "1" showing the order of the schedule in a schedule display unit 711 (to be described later).

Here, the schedule display unit 711 displays the schedule of the registration pattern, and displays the order of the process and the rack number corresponding to the order.

In addition to "1" as the order of the schedule, "2", "3", and the identification name associated with the registration pattern are displayed so as to respectively show that the registration pattern corresponding to the rack to be applied to the subsequent analysis is allocated. This drawing illustrates that the rack number 2 is analyzed for the first time, and thereafter, the rack numbers 3, 1, and 5 are analyzed for the second, third, and fourth times.

In order to confirm the content of the scheduled registration pattern, the operator uses the mouse 118a to select the display of the schedule number or the identification name, and can display the content of the registration pattern. If the analysis is requested, the registration pattern required for the analysis is searched and inquired for each analysis item. The registration pattern having the set specimen and the installation position are associated with each other, thereby determining the schedule. The order to be scheduled may be manually determined by the operator, or can be automatically determined by the device. Furthermore, a transferring mechanism can be disposed which automatically installs the specimen container 103 in the specimen rack 102.

In addition, similarly to the description above in FIG. 6, if the operator uses the mouse 118a to select the analysis result display button 710, the obtained analysis result or the device state can be displayed. It is also possible to easily cause the screen to return to the original screen.

As means for allowing the operator to more easily recognize the device state and the applied registration pattern, the following structures can be applied thereto. A color of the screen may be changed in order to clearly show whether the registration pattern displayed on the display unit 118c is the registration pattern under the analysis or the scheduled registration pattern to be applied to the subsequent analysis. In addition, the screen may be divided laterally or vertically. In this manner, the registration pattern under the analysis may be displayed on the left side or on the upper side, and the scheduled registration pattern to be applied to the subsequent analysis may be displayed on the right side or on the lower side. The above-described structures are not necessarily simultaneously mounted thereon. It is apparent that an advantageous effect is achieved even if the above-described structures are appropriately selected and combined with each other. In this manner, it is possible to perform continuous analysis on many and various specimens.

A third state is an operation state of returning to the standby state. The device completes the requested analysis, and the analysis results are sequentially output. Simultaneously, the device state is initialized such as cleaning or discarding the reaction container 104, and operations for returning to the standby position of each mechanical device. In this case, the specimen container 103 can be newly installed in the device, and the device can newly perform the analysis request. Accordingly, the registration content can be confirmed, changed, or applied. Alternatively, considering that the analysis result are still outputting, it is possible to change the content of the corresponding registration pattern, and it is possible to restrict the application of the registration pattern different therefrom.

The operator can install the specimen in the specimen rack 102. After registering the analysis request item, the operator can instruct the device to start the analysis.

Here, FIG. 15 is a view for describing the confirmation of the registration pattern on the display unit according to the present embodiment. As illustrated in FIG. 15, when the analysis starts, a registration pattern information display unit 1510 is disposed on a screen which displays a start button 1509 for instructing to start the analysis so that the operator can finally confirm the analysis request item or the applied registration pattern. The registration pattern information display unit 1510 here displays the registration pattern (illustrated as the rack number in the drawing), the registration content at each installation position, and the detailed information. As a display method of the start button 1509 and the registration pattern information display unit 1510, all can be displayed on the same screen, or all can be sequentially switched therebetween and displayed thereon. In addition, as illustrated in FIG. 15, the blocks can be visualized by coloring so that the classification for each block of the registration pattern can be easily confirmed.

According to the above-described embodiment, without replacing the specimen rack 102 installed in the automatic analysis device, it is possible to register the specimens, the number of which is more than the containing number of the specimen containers 103 in a single specimen rack 102. In addition, it is possible to instantaneously call up the registration information. Therefore, it is possible to efficiently perform the analysis process on many and various specimens.

Furthermore, the automatic analysis device according to the present embodiment can have an additional function for causing a timer to automatically set the registration pattern, or for automatically triggering an operation in a case where power is supplied to the device.

It is assumed that a type of the specimen used in a clinical laboratory varies depending on the date, the day of the week, and the season. For example, in a case where the specimen used on each day of one week is substantially fixed, the more efficient operation can be achieved by providing a function to automatically select and set the registration pattern of the specimen rack 102 corresponding to the content in accordance with the day of the week when the power is supplied to the device. For example, on Monday morning when the states of the device, the specimen, and the reagent are frequently confirmed, the registration pattern having increased installation positions of the calibrator is prepared in advance in order to perform many calibrations. In this manner, the registration pattern can be automatically applied. On Tuesday to Friday when many general specimens are carried into a laboratory, the registration pattern having increased installation positions of the general specimen is prepared in advance. In this manner, the registration pattern can be automatically applied. In a case where timing to confirm analysis performance by using the quality control sample is set in the afternoon of each day of the week, the registration pattern having increased installation positions of the quality control sample is prepared in advance. In this manner, the registration pattern can be automatically applied. In addition, when the power is supplied to the device every morning, the registration pattern having increased installation positions of the calibrator or the quality control sample is prepared in advance. In this manner, the registration pattern can be automatically applied. According to this configuration, it is possible to save the time for setting the device.

A plurality of specimen racks 102 can be disposed. The registration pattern can be input to each specimen rack 102, can be confirmed, and can be applied. According to this configuration, it is possible to perform the analysis process on more and various specimens.

Second Embodiment

In the first embodiment, an example of the automatic analysis device has been described in which a single analysis method for the biochemical analysis or the blood coagulation analysis is used or the mixed registration pattern is prepared.

In the present embodiment, an example of an automatic analysis device will be described in which a plurality of analysis methods for the biochemical analysis or the blood coagulation analysis are used so as to utilize the registration pattern having divided installation positions of the specimen.

FIG. 5 is a view for describing the preparation of the registration pattern on a display unit according to the present embodiment. Here, in an identification information display unit 508, a name of "Routine 2 (biochemistry/coagulation)" is registered in "Registration Pattern 3" which is an identification name of the third registration pattern in a registration pattern display unit 501. In addition to the items of the major classification, grouping (biochemistry and coagulation in this example) using the analysis method is additionally employed here.

The specimens required for the biochemical analysis are registered for the installation positions 1 to 50, and the specimens required for the blood coagulation analysis are registered for the installation positions 56 to 97. The installation places are divided for each analysis method in this way, thereby enabling the operator to easily identify the installation position and the specimen associated with the analysis method. For example, in a case where the installation positions of the specimens of the specimen rack 102 are respectively 55 on the inner peripheral side and 55 on the outer peripheral side, that is, 110 in total, the outer periphery corresponding to the installation positions 1 to 55 is allocated to the biochemical analysis, and the inner periphery corresponding to the installation positions subsequent to the installation position 56 is allocated to a common section of the blood coagulation analysis and both the analysis methods for the cleaning solution and the urgent specimen. In this manner, the operator can visually perform the scheduled analysis, and can confirm whether to deal with the specimen actually installed in the specimen rack 102. Therefore, the operator can accurately install the specimen.

In addition, it is conceivable to improve device performance by associating the device configuration, the device operation, the result display, and the result management with the installation position of the specimen according to each analysis method. As this example, a plurality of ring-shaped circular racks having different diameters are concentrically arranged, and the respective circular racks are grouped for each analysis method, thereby enabling the blocks to be allocated. The specimens of the different analysis method are installed in the inner peripheral and outer peripheral circular racks, thereby causing the device to perform any one analysis. Even in a case where the specimen dispensing probe 101 continuously collects the specimens from the circular racks, the collection of the specimens is not disturbed. The operator can install a newly generated specimen according to the different analysis method, and can start to perform the analysis. In this way, according to the device which can simultaneously process the plurality of analysis methods, a case is considered where the generating frequency or quantity of the specimens may vary. However, according to the present invention, without stopping the device, the analysis using the plurality of analysis methods can be continued, started, and completed. Therefore, it is possible to efficiently use the device.

Third Embodiment

In the present embodiment, an automatic analysis device will be described which can automatically allocate consecutive position numbers for each classification of the specimens in preparing the registration pattern.

FIG. 8 is a view for describing the preparation of the registration pattern on a display unit according to the present embodiment.

In FIG. 8, the display unit 118c displays the specimen rack 102 in a specimen disk information display unit 810, a frame of a solid line or a dotted line for indicating the installation position of the specimen on the specimen rack 102, and a type of the specimen indicated by the frame. The registration pattern illustrated in FIG. 8 has the same content as the registration pattern described above with reference to FIG. 5. The installation positions are divided for the biochemical analysis and the blood coagulation analysis. The respective frames to which a type of the specimen is allocated can be set one by one. If the button of the mouse 118a is pressed down at the start installation position and the mouse 118a is dragged to the end installation position and released, the installation positions therebetween are displayed while being surrounded by the frame. If each frame is similarly set, the registration pattern of the specimen rack 102 can be input. The registration pattern is set for each of "Registration Pattern 1" and "Registration Pattern 2" which are the identification names, and an application button 806 is selected by using the mouse 118a. In this manner, a desired registration pattern can be applied to the device. According to this configuration, consecutive position numbers for each classification of the specimen can be automatically allocated. It is possible to prevent mixing such as interruption of the calibrator between the position numbers to which the different classification, for example, the general specimen is allocated. Therefore, it is possible to prevent the operator from erroneously operating the device.

Fourth Embodiment

In the present embodiment, an example of the specimen rack including a display lamp will be described.

FIG. 9 is a view illustrating a basic configuration of the specimen rack according to the present embodiment. In FIG. 9, a display lamp 21 corresponding to each installation position of the specimen container 103 of the specimen rack 102 is disposed outside the specimen rack 102. The specimen rack 102 includes the display lamp 21 corresponding to the outer periphery of the specimen rack 102 and a display lamp 22 corresponding to the inner periphery. A position where a name number of the installation position of the specimen rack and a name number of the display lamp 21 are correlated with each other is set to an origin position of the rotation operation of the specimen rack 102.

In a state where the specimen rack 102 is caused to return to and stop at the origin position, a type of the specimen registered to each installation position can be displayed by using a lighting method such as coloring, turning-on, turning-off, and flashing of the display lamp 21. In addition, at any position where the specimen rack 102 stops other than the origin position, the display lamp 21 corresponding to the installation position of the specimen rack 102 is turned on. In this manner, the registration content can be displayed. According to this configuration, the operator can understand a type of the specimen applied in the display unit 118c. Furthermore, the operator can confirm the specimen on the device, and thus, it is possible to prevent the operator to install the specimen which is different from that of the registered content.

As a modification example for achieving the same advantageous effect as that of the display lamp, a sheet for displaying the content of the registration pattern may be installed in a central portion on the specimen rack 102 (not illustrated). A different sheet for each registration pattern is prepared, and the operator installs the sheet corresponding to the set registration pattern. In this manner, the operator can reduce the risk of erroneously recognizing the installation position of the specimen. Not only the registration pattern but also the detailed item can be recorded and displayed on the sheet if necessary. Therefore, it is possible to more efficiently operate the device.

Fifth Embodiment

In the present embodiment, an example of the specimen rack including an identification member will be described.

FIG. 10 is a view illustrating a basic configuration of the specimen rack according to the present embodiment. Identification members 1001a to 1001f having identification information for determining the block are installed at respective installation positions of the specimen container 103 of the specimen rack 102. In the present embodiment, as illustrated in FIG. 10, the operator installs the identification members 1001a to 1001f having the identification information indicating a start position of the block with regard to a type of the specimen, for the specimen rack 102. The operator transmits an instruction to start a block determination operation to the control unit 120, and causes the display unit 118c to display the instruction. The specimen rack 102 is rotated, and a barcode reader 124 installed at the inner peripheral and outer peripheral reading positions reads the identification information of the identification members 1001a to 1001f respectively installed on the outer periphery and the inner periphery. The identification information of the identification members 1001a to 1001f and the information of the installed position are linked to each other, and are stored in the storage unit 119 (refer to FIG. 1).

In this case, as long as the specimen rack 102 is rotated at passing speed which enables the identification information to be read, the specimen rack 102 can be rotated without being stopped. In addition, if necessary, the specimen rack 102 may be temporarily stopped at a position where the barcode reader reads the identification information.

FIG. 10 illustrates that the identification member 1001a located at the installation position No. 1 is a start position of the block of the quality control sample, and that the identification member 1001b located at the installation position No. 3 is a start position of the block of the calibrator. Subsequently, FIG. 10 illustrates that the identification members 1001c to 1001e installed at the installation positions Nos. 10, 21, and 30 are similarly start positions of the respectively corresponding blocks.

The barcode reader 124 may be used in common for use in reading the specimen information. The obtained identification information and the information relating to the installation position are calculated by the control unit 120, and are registered as the registration pattern of a new block. In this case, the number of the registration pattern can be simultaneously input. The registration pattern is displayed on the display unit 118c, and thus, the operator can confirm the content.

The identification members 1001a to 1001e are provided with characters, colors, and symbols which can be discriminated by the operator, thereby enabling the operator to easily understand whether the blocks are arranged as intended when the blocks are registered. Furthermore, even under the analysis, the operator can leave the installed identification members without any change. In this case, in order to prevent the specimen dispensing probe 101 from erroneously performing the dispensing operation, the control unit 120 correctly controls the specimen dispensing probe 101, based on that recorded information indicating that the identification member for identifying the installation position is installed at the corresponding installation position.

In addition, the installation position of the specimen is not occupied by only the identification member 1001 for identifying the installation position. In order to register the block according to the present embodiment described above, a dedicated identification member installation position 125 for installing an identification member 1002 having the identification information can be installed. An adapter configured to have a shape which does not interfere with the installation of a test tube and having the identification information printed thereon can also be attached by using a structure of the installation position of the test tube.

FIG. 10 illustrates that the identification member installation position 125 corresponds to only the installation position No. 1. Although others are omitted, the identification members can be disposed so as to correspond to each installation position. The operator can dispose the identification member at the identification member installation position 125, and can prepare the registration pattern classified into the block as intended. In addition, the operator can use the identification member installation position 125 as a marker when the specimen is installed.

The registration pattern registered to the device or applied to the device is displayed on a screen of the display unit 118c. The operator can easily confirm the content through the screen.

In addition, in a case where the blocks of any registration pattern are changed on the screen, the device reads the identification of the identification members 1001a to 1001f installed in the specimen rack 102. In a case where both the blocks have a difference, the device issues a warning to the operator. In this manner, the operator takes any countermeasure of correcting the block through the screen, correcting the installation position of an identification component of the specimen rack 102, and correcting both of these so that the contents match each other.

Sixth Embodiment

In the above-described embodiment, the unit in which the blocks can be registered is set to all of the specimen racks 102. In the present embodiment, a case will be described where a single specimen rack 102 is divided into a smaller regions and the block as the registration pattern can be registered to each region.

An operator can freely set this region. For example, a case is conceivable where an independent region is set on the inner periphery and the outer periphery in the specimen rack 102. Here, the operator selects and registers the calibrator, the quality control sample, and the general specimen on each of the inner periphery and the outer periphery, and prepares the registration pattern.

That is, for example, in a status where different analysis methods are simultaneously performed so that the inner periphery is allocated to the biochemical analysis and the outer periphery is allocated to the coagulation time analysis, the specimens required for the mutual analyses do not need to be replaced with each other, and the installation and operation can be performed. Therefore, it is possible to minimize the risk of erroneously selecting the installation place of the specimen.

In addition, as another example, in a case where the number of analyses is relatively small such as when the specimen can be sufficiently processed by allocating some of the specimen rack 102 to the general specimen, and in a case where there are many opportunities to perform various analyses and accordingly there are many opportunities to use various calibrators, the operator can allocate the inner periphery to the calibrators, and can allocate the outer periphery to the general specimen and the quality control sample. Therefore, the operator can effectively use the device.

In order to use a new calibrator, the registration pattern on the inner periphery may be newly prepared, or the existing registration content may be changed. The registration pattern on the outer periphery does not need to be changed. Therefore, the operator can deal with the analysis by carrying out minimum work.

In addition, the device can be set in order to preferentially analyze any one of regions into which the specimen rack 102 is divided or in order to analyze each region by determining the order in a case where the specimen rack 102 is divided into three or more regions. In this manner, in a case where it is complicated to organize the numerical order of the installation positions allocated to the specimen rack 102 or to allocate the detailed order to each registered specimen, the operator can more efficiently operate the device.

Seventh Embodiment

In the present embodiment, an example of the automatic analysis device will be described which is provided with a function to detect an error (hereinafter, simply referred to as an error detecting function in some cases) when the registration patterns are switched to each other in a case where a plurality of analyses are performed.

When the operator switches the registration patterns of the specimen rack 102, if there is the specimen installed in the specimen rack 102 without any change, the following case may occur. In this case, there is a problem in that the operator does not clearly recognize whether the specimen is installed so as to match the registration pattern before the specimen is switched or otherwise whether the specimen is installed so as to match the registration pattern after the specimen is switched. The present embodiment corresponds to the case.

FIG. 14 is a flowchart illustrating an operation for detecting an error when the registration patterns are switched in the automatic analysis device according to the present embodiment.

In Step 1401, the previous analysis result is output (S1401).

Next, in Step 1402, new analysis content is requested (S1402). In Step 1403, it is determined whether the registration pattern required for the requested analysis content us selected (S1403). As described above, the operator can select the registration pattern via the operation unit 118.

Here, in a case where the required registration pattern is selected, in Step 1404, it is determined whether or not to confirm the presence or absence of the specimen on the rack (S1404). In a case where the confirmation is required, the process proceeds to the process subsequent to Step 1406 (to be described later). In a case where the confirmation is not required, the process proceeds to Step 1411, and the requested analysis content is fetched or input (S1411).

On the other hand, in a case where the required registration pattern is not selected, in Step 1405, the registration pattern is changed (S1405). In Step 1406, the presence or absence of the specimen on the rack is confirmed (S1406). Specifically, the confirmation is performed by rotating the specimen rack 102 and causing a detector (not illustrated) to determine the presence or absence of the specimen of the specimen rack 102 at the installation positions on the inner periphery and the outer periphery along the rotation direction. Here, the barcode reader 124 installed instead of the detector or together with the detector may read the identification information. The barcode reader 124 may not only determine the presence or absence of the specimen, but also may determine whether the specimen matches the registration pattern.

Here, if the specimen is not installed on the rack, the analysis content requested in Step 1411 is fetched or input (S1411). On the other hand, in a case where the specimen is installed on the rack, in Step 1408, it is determined whether the installed specimen is the analysis target (S1408). The determination is performed by confirming whether the installed specimen matches the registration pattern before switching or whether the installed specimen matches the selected registration pattern after switching.

As a result of the confirmation, in a case where the installed specimen is the analysis target, the analysis content requested in Step 1411 is fetched or input (S1411). In this case, it is assumed that the installed specimen is a retest object. On the other hand, in a case where the specimen is not the analysis target, in Step 1409, an operator's attention is called (S1409). Here, calling the operator's attention includes various methods. However, for example, a method may be used in which calling the operator's attention is displayed on the screen of the display unit 118c so as to indicate the specimen is a risk factor which may cause an analysis error.

In the above-described example, a case has been described where the operator's attention is not called in a case where the installed specimen is the analysis target. In this case, analysis efficiency can be improved, and throughput can be increased. However, in a case where the installation of the specimen is confirmed in Step 1407, the operator's attention can be first called before the process proceeds to Step 1408. In this case, the operator can more carefully confirm the specimen.

Furthermore, in addition to the above-described example, as a result of the confirmation in Step 1408, in a case where the installed specimen is not the analysis target, setting can also be made so as not to call the operator's attention. For example, it is desirable that the cleaning solution or the specimen dilution is always installed in the specimen rack 102. Therefore, according to this configuration, it is possible to prevent the device from calling unnecessary attention.

Referring back to the flowchart in FIG. 14, the operator receives the attention in Step 1409, and confirms the specimen. If the remaining specimen is the specimen which is unintentionally left, in Step 1410, the operator can instruct the device to remove this specimen (S1410). In this manner, the specimen installed in the rack can match the content of the analysis request. Here, the device can automatically perform a removing operation of the specimen by omitting Step 1409.

In Step 1412, based on the analysis content (the required specimen and the installation position corresponding thereto) fetched or input in Step 1411, the operator installs the specimen at the corresponding position on the rack (S1412). After the installation, the analysis is performed in Step 1413 (S1413), and the analysis result obtained in Step 1414 is output (S1414).

Here, the detector for detecting the presence or absence of the specimen on the above-described reagent rack 102 or the barcode reader 124 reads the identification information by setting only the installation position used for the new analysis as a confirmation target. Accordingly, the confirmation time can be shortened. In addition, a time needed to remove the specimen remaining at the other installation position and operator's labor can be omitted. That is, analysis throughput can be improved.

In addition, timing at which the operation starts in order to confirm the presence or absence of the specimen in Step 1407 can be set any timing except for timing immediately after the registration pattern is changed in Step 1405. For example, if the timing is in a stage before the device restarts the analysis operation after the operator instructs the device to restart the analysis though the operation unit 118, setting can be made so that the operation sequence for confirming the presence or absence is performed at the other timing. Various forms can be set depending on the preference of the operator who considers that it is inefficient to remove the specimen remaining before the registration pattern is changed, or in accordance with the configuration of the operation unit 118.

In addition, the device configuration which can set the region into which the above-described specimen rack 102 is divided can be combined with the device configuration which detects the specimen remaining in the specimen rack 102 when the registration patterns are switched. The specimens are evenly installed in the specimen rack 102, and the analysis is performed. Before the analysis is completed, that is, before all of the specimens are aspirated and collected by the specimen dispensing probe 101 in accordance with the analysis request, the specimen which needs to be newly analyzed for the interrupting analysis is brought in. Determining that the specimen is the calibrator which is not present in the current registration pattern, the operator first completes the analysis of the calibrator generated due to the interrupting analysis. Thereafter, the operator desires to restart the analysis of the specimen on which the analysis is not completed yet while leaving the specimen installed in the specimen rack 102. In order to effectively deal with this status, the specimen rack 102 is divided into the regions of the inner periphery and the outer periphery. In this manner, a configuration is adopted in which any registration pattern before switching is mainly prepared for the general specimen. The analysis of the specimen installed in advance starts from the inner periphery, and the sampling of the specimen is stopped in the middle of the outer periphery. Here, in order to analyze the interrupted calibrator, the specimen which remains on the inner periphery and on which the analysis is completed is removed. Thereafter, only the registration pattern on the inner periphery is changed to the registration pattern corresponding to the calibrator. In this way, it is not necessary to change the registration pattern on the outer periphery. If the operation is performed in order to detect mismatching between the specimen remaining in the specimen rack 102 and the registration pattern after switching, the mismatching on the inner periphery is detected beforehand. The specimen remaining on the outer periphery is not regarded as a problem. According to this configuration, after the specimen remaining on the inner periphery is analyzed, the analysis of the specimen remaining on the outer periphery can automatically restart. Therefore, the analysis efficiency can be further improved.

In this way, in a case where the registration pattern in a certain region of the specimen rack 102 is changed, setting can be made so as to preferentially analyze the specimen installed in the region. According to this configuration, as described above, it is possible to preferentially analyze not only the calibrator but also the quality control sample or the urgent specimen, regardless of a type of the specimens. Therefore, the device can be more efficiently operated.

REFERENCE SIGNS LIST 10, 11, 12 INSTALLATION POSITION
21, 22 DISPLAY LAMP
100 AUTOMATIC ANALYSIS DEVICE
101 SPECIMEN DISPENSING PROBE (SAMPLE DISPENSING MECHANISM)
102 SPECIMEN RACK

103 SPECIMEN CONTAINER (SAMPLE CONTAINER)
104 REACTION CONTAINER
105 SPECIMEN SYRINGE PUMP
106 REAGENT DISPENSING PROBE (REAGENT DISPENSING MECHANISM)
107 REAGENT RACK
108 REAGENT CONTAINER
109 REAGENT TEMPERATURE RAISING MECHANISM
110 REAGENT SYRINGE PUMP
111 REACTION CONTAINER STOCK UNIT
112 REACTION CONTAINER CONVEYANCE UNIT
113 DETECTION UNIT
114 REACTION CONTAINER INSTALLATION UNIT
115 LIGHT SOURCE
116 DETECTION UNIT (OPTICAL SENSOR)
117 REACTION CONTAINER DISCARD UNIT
118 OPERATION UNIT
118a MOUSE
118b KEYBOARD
118c DISPLAY UNIT
119 STORAGE UNIT
120 CONTROL UNIT
120a OVERALL CONTROL UNIT
120b MEASUREMENT CONTROL UNIT
121 A/D CONVERTER
122 INTERFACE
123 PRINTER
124 BARCODE READER
125 IDENTIFICATION MEMBER INSTALLATION POSITION
301, 401, 501, 601, 701, 801, 1501 REGISTRATION PATTERN DISPLAY UNIT
302, 402, 502, 602, 702 SPECIMEN INFORMATION UNIT
303, 403, 503, 603, 703 DETAILED ITEM DISPLAY UNIT
304 REGISTRATION LIST DISPLAY UNIT
305 INSTALLATION POSITION ALLOCATION DISPLAY UNIT
306, 406, 506, 606, 706, 806 APPLICATION BUTTON
307 DETAILED ITEM SETTING TARGET DISPLAY UNIT
308, 408, 508, 608, 708 IDENTIFICATION NUMBER DISPLAY UNIT
609, 709, 809 STATUS DISPLAY UNIT
610, 710, 810 ANALYSIS RESULT DISPLAY UNIT
1001 IDENTIFICATION MEMBER
1509 (ANALYSIS) START BUTTON
1510 REGISTRATION PATTERN INFORMATION DISPLAY UNIT

The invention claimed is:

1. An automatic analysis device, comprising:
a reaction container;
a plurality of samples having different classifications;
a plurality of containers that contain a plurality of samples having different classifications;
one sample rack having a plurality of installation positions configured to hold the containers, the installation positions disposed at predetermined locations on the one sample rack;
a detection unit including a light source and an optical sensor configured to measure transmitted or scattered light from the sample in the reaction container;
a first dispensing probe; and
a control unit programmed to:
store a plurality of different registration patterns, each having a plurality of respective blocks to indicate arrangements of the containers to be held on the one sample rack,
receive, from an operator, respective first information for each of the blocks of each the plurality of registration patterns, the respective first information indicating a respective classification and a respective number of the installation positions which correspond to the respective classification for a respective one of the blocks,
automatically allocate, respective second information for each of the blocks of each of the plurality of registration patterns, the respective second information indicating a respective start position and a respective end position corresponding to the respective number of the installation positions in the respective first information for the respective one of the blocks,
receive, from the operator, a selection of one registration pattern from the plurality of registration patterns,
instruct the operator to install the containers at the installation positions of the one sample rack according to the first information and the second information of the selected registration pattern to apply the selected registration pattern to the one sample rack,
confirm, via input by the operator, that the selected registration pattern is applied to the one sample rack,
upon confirming the selected registration pattern has been applied to the one sample rack, control the dispensing probe to transfer one of the samples installed on the one sample rack to the reaction container, and
control the detection unit to analyze the sample in the reaction container,
wherein the registration patterns correspond to a plurality of types of methods for analyzing the sample including a calibration method, a first routine analysis method, and a second routine analysis method including biochemical analysis and blood coagulation analysis, and
wherein the different classifications include at least one of quality control samples, calibrators, pretreatment liquids, general samples, retest samples, factor deficient plasmas, cleaning solutions, and urgent samples.

2. The automatic analysis device according to claim 1, further comprising:
a second dispensing probe,
wherein the control unit is programmed to:
control the second dispensing probe to transfer a reagent to the reaction container, and
control the detection unit to analyze a reaction solution of the sample and the reagent in the reaction container.

3. The automatic analysis device according to claim 1, further comprising:
a display unit that displays information relating to an analysis of the sample,
wherein the control unit is programmed to control the display unit to display content of the selected registration pattern applied to the one sample rack together with a start button selectable to instruct the control unit to start the analysis of the sample.

4. The automatic analysis device according to claim 1, further comprising:
a display unit that displays information relating to an analysis of the sample,
wherein the control unit is programmed to control the display unit to always display a plurality of buttons selectable to input the selection of the one registration pattern applied to the one sample rack or information of the selected registration pattern.

5. The automatic analysis device according to claim 1,
wherein the control unit is programmed to automatically allocate the respective start position and the respective end position so that the respective classification corresponds to the installation positions which are consecutive on the one sample rack.

6. The automatic analysis device according to claim 1,
wherein the installation positions of the one sample rack include a plurality of outer peripheral installation positions and a plurality of inner peripheral installation positions, and
wherein the control unit is programmed to prepare and store the registration patterns for each of the types of the methods for analyzing the sample so that the containers are respectively loaded at the outer peripheral installation positions and the inner peripheral installation positions.

7. The automatic analysis device according to claim 1,
wherein, for each of the registration patterns, the respective classification is different for each of the blocks.

8. The automatic analysis device according to claim 7,
wherein the control unit is programmed to automatically allocate the respective start position and the respective end position to define the installation positions which are consecutive from the respective start position to the respective end position on the one sample rack.

9. The automatic analysis device according to claim 1,
wherein the control unit is programmed to receive a schedule indicating an order for applying two or more of the registration patterns to the one sample rack.

10. The automatic analysis device according to claim 1,
wherein one of the classifications is urgent samples,
wherein the second information indicates the respective start position and the respective end position corresponding to the respective number of the installation positions for the respective block which corresponds to the urgent samples and which are separate from the other respective blocks for each of the registration patterns.

11. The automatic analysis device according to claim 1,
wherein one of the classifications is cleaning solutions and another one of the classifications is pretreatment liquids, and
wherein the second information indicates the respective start position and the respective end position corresponding to the respective number of the installation positions for the respective blocks which correspond to the cleaning solutions and the pretreatment liquids and which are separate from the other respective blocks for each of the registration patterns.

12. The automatic analysis device according to claim 4, further comprising:
another reaction container,
wherein the control unit is programmed to:
when the selected registration pattern is changed to another one of the registration patterns, instruct the operator to install the containers at the installation positions of the one sample rack according to the first information and the second information of the other one of the registration patterns to apply the selected other one of the registration patterns to the one sample rack,
confirm whether the other one of the registration patterns is applied to the one sample rack, and
when the other one of the registration patterns has been applied to the one sample rack, control the dispensing probe to transfer another one of the samples to the other reaction container, and
control the detection unit to analyze the sample in the other reaction container.

13. The automatic analysis device according to claim 12,
wherein the control unit is programmed to, when one or more of the containers are absent at the corresponding installation positions in the one sample rack in accordance with the other one of the registration patterns, control the display unit to display a warning.

14. The automatic analysis device according to claim 1,
wherein one of the classifications is factor deficient plasma.

15. The automatic analysis device according to claim 1,
wherein the control unit is programmed to allocate detailed information of the samples installed to one or more of the respective installation positions included in at least one of the blocks of at least one of the plurality of registration patterns.

16. The automatic analysis device according to claim 15,
wherein the control unit is programmed to allocate detailed information of the samples installed to two or more of the respective installation positions included in at least one of the blocks of two or more of the registration patterns.

17. The automatic analysis device according to claim 1, further comprising:
a display unit that displays information relating to an analysis of the sample,
wherein the control unit is programmed to control the display unit to instruct the operator by displaying a schematic diagram for schematically displaying a configuration of the selected registration pattern including colors or symbols which identify the installation positions of each of the blocks of the selected registration pattern.

18. The automatic analysis device according to claim 1, further comprising:
a display unit that displays information relating to an analysis of the sample,
wherein the control unit is programmed to control the display unit to instruct the operator by displaying a schematic diagram for schematically displaying a configuration of the selected registration pattern including colors or symbols which identify the installation positions in accordance with the first information and the second information of the selected registration pattern.

19. The automatic analysis device according to claim 1, further comprising:
a barcode reader disposed next to the one sample rack,
wherein the one sample rack has a plurality of barcodes disposed thereon, and
wherein the control unit is programmed to receive the respective first information by reading the respective barcodes to determine the respective number of the installation positions for each of the registration patterns.

20. The automatic analysis device according to claim 19,
wherein respective installation positions of the barcodes are predetermined to correspond to the respective installation positions configured to hold the containers, and the installation positions of the barcodes are disposed separate from the installation positions configured to hold the containers.

21. An analysis method in an automatic analysis device having one sample rack having a plurality of installation positions configured to hold a plurality of containers that contain a plurality of samples having different classifications, the method comprising:
- storing a plurality of different registration patterns, each having a plurality of respective blocks to indicate arrangements of the containers to be held on the one sample rack;
- receiving, from an operator, respective first information for each of the blocks of each of the plurality of registration patterns, the respective first information indicating a respective classification and a respective number of the installation positions which correspond to the respective classification for a respective one of the blocks;
- automatically allocating, respective second information for each of the blocks of each of the plurality of registration patterns, the respective second information indicating a respective start position and a respective end position corresponding to the respective number of the installation positions in the respective first information for the respective one of the blocks;
- receiving, from the operator, a selection of one registration pattern from the plurality of stored registration patterns;
- instructing the operator to install the containers at the installation positions of the one sample rack according to the first information and the second information of the selected registration pattern to apply the selected registration pattern to the one sample rack;
- confirming, via input by the operator, that the selected registration pattern is applied to the one sample rack;
- upon confirming the selected registration pattern has been applied to the one sample rack, controlling a dispensing probe to transfer one of the samples installed on the one sample rack to a reaction container; and
- controlling a detection unit to analyze the sample in the reaction container,
- wherein the registration patterns correspond to a plurality of types of methods for analyzing the sample including a calibration method, a first routine analysis method, and a second routine analysis method including biochemical analysis and blood coagulation analysis,
- wherein the different classifications include at least one of quality control samples, calibrators, pretreatment liquids, general samples, retest samples, factor deficient plasmas, cleaning solutions, and urgent samples.

* * * * *